(12) United States Patent
Kreif et al.

(10) Patent No.: US 11,737,930 B2
(45) Date of Patent: Aug. 29, 2023

(54) CONFIGURABLE SINGLE TRANSFER INSERT PLACEMENT METHOD AND APPARATUS

(71) Applicant: Curt G. Joa, Inc., Sheboygan Falls, WI (US)

(72) Inventors: Lloyd F. Kreif, Sheboygan Falls, WI (US); Darren Horness, Sheboygan, WI (US); Brian Nelson, Sheboygan, WI (US); Collin M. Heinz, Plymouth, WI (US); Kevin D. Blank, Port Washington, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 308 days.

(21) Appl. No.: 16/803,183

(22) Filed: Feb. 27, 2020

(65) Prior Publication Data

US 2021/0267812 A1  Sep. 2, 2021

(51) Int. Cl.
*A61F 13/15* (2006.01)
*B65H 39/14* (2006.01)

(52) U.S. Cl.
CPC ....... *A61F 13/15764* (2013.01); *B65H 39/14* (2013.01); *A61F 13/15723* (2013.01);
(Continued)

(58) Field of Classification Search
CPC ......... A61F 13/15764; A61F 13/15763; B65H 39/14; B65H 29/241; B65H 2406/3454
See application file for complete search history.

(56) References Cited

U.S. PATENT DOCUMENTS

| 135,145 A | 1/1873 | Murphy |
| 293,353 A | 2/1884 | Purvis |

(Continued)

FOREIGN PATENT DOCUMENTS

| BE | 1007854 A3 | 11/1995 |
| CA | 1146129 A | 5/1983 |

(Continued)

OTHER PUBLICATIONS

USPTO Restriction Requirement dated Apr. 8, 2010, regarding U.S. Appl. No. 12/070,879, 9 pages.

(Continued)

*Primary Examiner* — George R Koch
*Assistant Examiner* — Christopher C Caillouet
(74) *Attorney, Agent, or Firm* — Klintworth & Rozenblat IP LLP

(57) ABSTRACT

A configurable cutting and transfer apparatus includes a cutter mechanism to cut an incoming web of material into a plurality of discrete articles and a transfer mechanism operable with the cutter mechanism to transfer and rotate the discrete articles from a web receiving location to an article placement location. The transfer mechanism includes a drive shaft rotatable about a transfer axis, a carriage plate mounted to the drive shaft so as to rotate therewith about the transfer axis, and a segmented puck wheel comprising a plurality of carriage units securable to, and repositionable on, the carriage plate so as to rotate therewith to travel along a transfer path about the transfer axis from the web receiving location to the pad placement location, each of the carriage units including a puck operable to provide a rotating and re-pitching of the articles between the web receiving location and the pad placement location.

23 Claims, 19 Drawing Sheets

(52) U.S. Cl.
CPC .................. B65G 2201/02 (2013.01); B65H 2301/33216 (2013.01); B65H 2801/57 (2013.01)

(56) References Cited

U.S. PATENT DOCUMENTS

| | | |
|---|---|---|
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,605,842 A | 11/1926 | Jones |
| 1,686,595 A | 10/1928 | Belluche |
| 1,957,651 A | 5/1934 | Joa |
| 2,009,857 A | 7/1935 | Adolph |
| 2,054,832 A | 9/1936 | Adolph |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Samuel et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,659,437 A | 11/1953 | Huck |
| 2,695,025 A | 11/1954 | Andrews |
| 2,702,406 A | 2/1955 | Glenn |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | George et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 5/1967 | Joa |
| 3,355,974 A | 12/1967 | Carmichael |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,491,651 A | 1/1970 | Pascoe |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,707,102 A | 12/1972 | Huppenthal et al. |
| 3,728,191 A | 4/1973 | Wierzba et al. |
| 3,751,224 A | 8/1973 | Wackerle |
| 3,758,102 A | 9/1973 | Munn |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,822,838 A | 7/1974 | Butler et al. |
| 3,847,273 A | 11/1974 | Buhayar |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Parish |
| 4,002,005 A | 1/1977 | Mueller et al. |
| 4,003,298 A | 1/1977 | Schott, Jr. |
| 4,009,626 A | 3/1977 | Gressman |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Hudon et al. |
| 4,168,776 A | 9/1979 | Hoeboer |
| 4,171,239 A | 10/1979 | Hirsch et al. |
| 4,205,679 A | 6/1980 | Brooks et al. |
| 4,208,230 A | 6/1980 | Magarian |

(56) References Cited

U.S. PATENT DOCUMENTS

| | | |
|---|---|---|
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,349,140 A | 9/1982 | Passafiume |
| 4,364,787 A | 12/1982 | Radzins |
| 4,374,576 A | 2/1983 | Ryan |
| 4,379,008 A | 4/1983 | Gross et al. |
| 4,380,484 A | 4/1983 | Repik et al. |
| 4,394,898 A | 7/1983 | Campbell |
| 4,411,721 A | 10/1983 | Wishart |
| 4,426,897 A | 1/1984 | Littleton |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,578,133 A | 3/1986 | Oshefsky et al. |
| 4,586,199 A | 5/1986 | Birring |
| 4,589,945 A | 5/1986 | Polit |
| 4,603,800 A | 8/1986 | Focke et al. |
| 4,606,964 A | 8/1986 | Wideman |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,625,612 A | 12/1986 | Oliver |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander et al. |
| 4,723,698 A | 2/1988 | Schoonderbeek |
| 4,726,874 A | 2/1988 | Vanvliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,757,732 A | 7/1988 | Arima |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | Angelo |
| 4,880,102 A | 11/1989 | Indrebo |
| 4,888,231 A | 12/1989 | Angstadt |
| 4,892,536 A | 1/1990 | Desmarais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons et al. |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,029,505 A | 7/1991 | Holliday |
| 5,045,039 A | 9/1991 | Bay |
| 5,045,135 A | 9/1991 | Meissner et al. |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack et al. |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner et al. |
| 5,223,069 A | 6/1993 | Tokuno et al. |
| 5,226,992 A | 7/1993 | Morman |
| 5,246,433 A | 9/1993 | Hasse et al. |
| 5,252,170 A | 10/1993 | Schaupp |
| 5,252,228 A | 10/1993 | Stokes et al. |
| 5,267,933 A | 12/1993 | Precoma |
| 5,273,228 A | 12/1993 | Yoshida et al. |
| 5,275,076 A | 1/1994 | Greenwalt |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai et al. |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,410,857 A | 5/1995 | Utley |
| 5,415,649 A | 5/1995 | Watanabe et al. |
| 5,417,132 A | 5/1995 | Cox et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,486,253 A | 1/1996 | Otruba |

(56) References Cited

U.S. PATENT DOCUMENTS

| | | |
|---|---|---|
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,520,875 A | 5/1996 | Wnuk et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,555,786 A | 9/1996 | Fuller |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,636,500 A | 6/1997 | Gould |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease et al. |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka et al. |
| 5,735,984 A | 4/1998 | Hoff et al. |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,766,411 A | 6/1998 | Wilson |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,494 A | 3/1999 | Hoff et al. |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,935,367 A | 8/1999 | Hollenbeck |
| 5,938,193 A | 8/1999 | Bluemle et al. |
| 5,938,652 A | 8/1999 | Sauer |
| 5,964,390 A | 10/1999 | Boerresen et al. |
| 5,964,970 A | 10/1999 | Woolwine et al. |
| 5,971,134 A | 10/1999 | Trefz et al. |
| 5,983,764 A | 11/1999 | Hillebrand |
| 6,009,781 A | 1/2000 | McNeil |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,080,909 A | 6/2000 | Oesterdahl et al. |
| 6,098,249 A | 8/2000 | Toney et al. |
| 6,123,792 A | 9/2000 | Samida et al. |
| 6,139,004 A | 10/2000 | Couillard et al. |
| 6,142,048 A | 11/2000 | Bradatsch et al. |
| 6,171,432 B1 | 1/2001 | Brisebois et al. |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye et al. |
| 6,210,386 B1 | 4/2001 | Inoue |
| 6,212,859 B1 | 4/2001 | Bielik et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Boerresen et al. |
| 6,280,373 B1 | 8/2001 | Lanvin |
| 6,284,061 B1 | 9/2001 | Inoue et al. |
| 6,284,081 B1 | 9/2001 | Vogt et al. |
| 6,287,409 B1 | 9/2001 | Stephany |
| 6,296,469 B1 | 10/2001 | Suzuki |
| 6,305,260 B1 | 10/2001 | Truttmann et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala et al. |
| 6,325,201 B1 | 12/2001 | Bailey et al. |
| 6,336,921 B1 | 1/2002 | Kato et al. |
| 6,336,922 B1 | 1/2002 | Vangompel et al. |
| 6,336,923 B1 | 1/2002 | Fujioka |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturing et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| RE38,033 E | 3/2003 | Okonski et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,550,517 B1 | 4/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | Vaneperen et al. |
| 6,596,107 B2 | 7/2003 | Stopher et al. |
| 6,596,108 B2 | 7/2003 | McCabe |
| 6,604,623 B2 | 8/2003 | Sumi et al. |
| 6,605,172 B1 | 8/2003 | Anderson et al. |
| 6,605,173 B2 | 8/2003 | Glaug et al. |
| 6,620,276 B1 | 9/2003 | Kuntze et al. |
| 6,634,269 B2 | 10/2003 | Eckstein et al. |
| 6,637,583 B1 | 10/2003 | Andersson |
| 6,648,122 B1 | 11/2003 | Hirsch et al. |

(56) References Cited

U.S. PATENT DOCUMENTS

| | | |
|---|---|---|
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann et al. |
| 6,743,324 B2 | 6/2004 | Hargett |
| 6,750,466 B2 | 6/2004 | Guha et al. |
| 6,758,109 B2 | 7/2004 | Nakakado |
| 6,766,817 B2 | 7/2004 | Da Silva |
| 6,779,426 B1 | 8/2004 | Holliday |
| 6,808,582 B2 | 10/2004 | Popp et al. |
| D497,991 S | 11/2004 | Otsubo et al. |
| 6,811,019 B2 | 11/2004 | Christian et al. |
| 6,811,642 B2 | 11/2004 | Ochi |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,718 B2 | 7/2005 | Ducker et al. |
| 6,918,404 B2 | 7/2005 | Dias Da Silva |
| 6,976,521 B2 | 12/2005 | Mlinar et al. |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,048,725 B2 | 5/2006 | Kling et al. |
| 7,066,586 B2 | 6/2006 | Da Silva |
| 7,069,970 B2 | 7/2006 | Tomsovic et al. |
| 7,077,393 B2 | 7/2006 | Ishida |
| 7,130,710 B2 | 10/2006 | Popp et al. |
| 7,137,971 B2 | 11/2006 | Tanzer |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner et al. |
| 7,214,174 B2 | 5/2007 | Allen et al. |
| 7,214,287 B2 | 5/2007 | Shiomi et al. |
| 7,220,335 B2 | 5/2007 | Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,793,772 B2 | 9/2010 | Schaefer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | Mccabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,025,652 B2 | 9/2011 | Hornung et al. |
| 8,062,459 B2 | 11/2011 | Nakakado et al. |
| 8,100,173 B2 | 1/2012 | Hornung et al. |
| 8,172,977 B2 | 5/2012 | McCabe et al. |
| 8,176,573 B2 | 5/2012 | Popp et al. |
| 8,178,035 B2 | 5/2012 | Edvardsson et al. |
| 8,182,624 B2 | 5/2012 | Handziak |
| 8,182,735 B2 | 5/2012 | Edvardsson |
| 8,182,736 B2 | 5/2012 | Edvardsson |
| 8,293,056 B2 | 10/2012 | McCabe |
| 8,381,489 B2 | 2/2013 | Freshwater et al. |
| 8,398,793 B2 | 3/2013 | Andrews et al. |
| 8,417,374 B2 | 4/2013 | Meyer et al. |
| 8,460,495 B2 | 6/2013 | McCabe |
| 8,512,496 B2 | 8/2013 | Makimura |
| 8,813,351 B2 | 8/2014 | Schoultz et al. |
| 9,550,306 B2 | 1/2017 | McCabe et al. |
| 2013/0239764 A1* | 9/2013 | McCabe ............... B26D 1/425 83/100 |

FOREIGN PATENT DOCUMENTS

| | | |
|---|---|---|
| CA | 1153345 A | 9/1983 |
| CA | 1190078 A | 7/1985 |
| CA | 1210744 A | 9/1986 |
| CA | 1212132 A | 9/1986 |
| CA | 1236056 A | 5/1988 |
| CA | 1249102 A | 1/1989 |
| CA | 1292201 C | 11/1991 |
| CA | 1307244 C | 9/1992 |
| CA | 1308015 C | 9/1992 |
| CA | 1310342 C | 11/1992 |
| CA | 2023816 C | 3/1994 |
| CA | 2330679 A1 | 12/1999 |
| CA | 2337700 A1 | 9/2001 |
| CA | 2404154 A1 | 10/2001 |
| CA | 2407867 A1 | 4/2003 |
| CA | 2600432 A1 | 9/2006 |
| CA | 2541194 A1 | 10/2006 |
| CA | 2559517 A1 | 4/2007 |
| CA | 2699136 A1 | 10/2010 |
| CA | 142627 S | 6/2013 |
| CN | 202105105 U | 1/2012 |
| DE | 60123502 T2 | 1/2007 |
| DE | 102005035544 A1 | 2/2007 |
| DE | 60216550 T2 | 4/2007 |
| DE | 102005048868 A1 | 4/2007 |
| DE | 102006047280 A1 | 4/2007 |
| DE | 102007063209 A1 | 6/2009 |
| EP | 0044206 A2 | 1/1982 |
| EP | 0048011 A1 | 3/1982 |
| EP | 0089106 A2 | 9/1983 |
| EP | 0099732 A2 | 2/1984 |
| EP | 0206208 A1 | 12/1986 |
| EP | 0304140 A2 | 2/1989 |
| EP | 0411287 A1 | 2/1991 |
| EP | 0439897 A1 | 8/1991 |
| EP | 0455231 A1 | 11/1991 |
| EP | 0510251 A1 | 10/1992 |
| EP | 0589859 A1 | 3/1994 |
| EP | 0652175 A1 | 5/1995 |
| EP | 0676352 A1 | 10/1995 |
| EP | 0811473 A2 | 12/1997 |
| EP | 0901780 A1 | 3/1999 |
| EP | 0990586 A2 | 4/2000 |
| EP | 0990588 A1 | 4/2000 |
| EP | 1132325 A1 | 9/2001 |
| EP | 1199057 A1 | 4/2002 |
| EP | 1366734 A1 | 12/2003 |
| EP | 1393701 A2 | 3/2004 |

(56) References Cited

FOREIGN PATENT DOCUMENTS

| | | |
|---|---|---|
| EP | 1415628 A1 | 5/2004 |
| EP | 1433731 A1 | 6/2004 |
| EP | 1571249 A2 | 9/2005 |
| EP | 1619008 A2 | 1/2006 |
| EP | 1707168 A2 | 10/2006 |
| EP | 1302424 B1 | 12/2006 |
| EP | 1801045 A1 | 6/2007 |
| EP | 1941853 A1 | 7/2008 |
| EP | 1961403 A2 | 8/2008 |
| EP | 1994919 A1 | 11/2008 |
| EP | 2103427 A2 | 9/2009 |
| EP | 2233116 A1 | 9/2010 |
| EP | 2238955 A1 | 10/2010 |
| EP | 1175880 B2 | 5/2012 |
| EP | 1868821 B1 | 1/2013 |
| EP | 1726414 B1 | 3/2013 |
| EP | 2036522 B1 | 3/2013 |
| EP | 1272347 B1 | 4/2013 |
| EP | 2032338 B1 | 8/2013 |
| EP | 2659869 A1 | 11/2013 |
| ES | 296211 A1 | 4/1964 |
| ES | 509706 A2 | 2/1983 |
| ES | 520559 A1 | 3/1984 |
| ES | 200601373 A | 1/2009 |
| ES | 2311349 A1 | 2/2009 |
| FR | 1132325 A | 3/1957 |
| FR | 1096373 A | 12/1967 |
| FR | 2177355 A5 | 11/1973 |
| FR | 2252961 A1 | 6/1975 |
| FR | 2255961 A1 | 7/1975 |
| FR | 2891811 A1 | 4/2007 |
| GB | 191101501 A | 1/1912 |
| GB | 439897 A | 12/1935 |
| GB | 856389 A | 12/1960 |
| GB | 941073 A | 11/1963 |
| GB | 1126539 A | 9/1968 |
| GB | 1346329 A | 2/1974 |
| GB | 1412812 A | 11/1975 |
| GB | 1467470 A | 3/1977 |
| GB | 2045298 A | 10/1980 |
| GB | 2115775 A | 9/1983 |
| GB | 2288316 A | 10/1995 |
| JP | H028364 A | 1/1990 |
| JP | H0428364 A | 1/1992 |
| JP | H0542180 A | 2/1993 |
| JP | H0576566 A | 3/1993 |
| JP | H0626160 A | 2/1994 |
| JP | H0626161 A | 2/1994 |
| JP | H06197925 A | 7/1994 |
| JP | H09299398 A | 11/1997 |
| JP | H1035621 A | 2/1998 |
| JP | H10277091 A | 10/1998 |
| JP | 2008161300 A | 7/2008 |
| SE | 0601003 L | 12/2006 |
| SE | 0601145 L | 12/2006 |
| SE | 0602047 L | 4/2007 |
| SE | 0601003 C2 | 6/2007 |
| SE | 0601145 C2 | 10/2009 |
| WO | WO1993015248 A1 | 8/1993 |
| WO | WO1994003301 A2 | 2/1994 |
| WO | WO1997023398 A1 | 7/1997 |
| WO | WO1997032552 A1 | 9/1997 |
| WO | WO1997047265 A1 | 12/1997 |
| WO | WO1997047810 A1 | 12/1997 |
| WO | WO1998021134 A1 | 5/1998 |
| WO | WO1998055298 A1 | 12/1998 |
| WO | WO1999007319 A1 | 2/1999 |
| WO | WO1999013813 A1 | 3/1999 |
| WO | WO9927876 A1 | 6/1999 |
| WO | WO1999032385 A1 | 7/1999 |
| WO | WO1999065437 A1 | 12/1999 |
| WO | WO2001043682 A1 | 6/2001 |
| WO | WO2001072237 A2 | 10/2001 |
| WO | WO2003031177 A1 | 4/2003 |
| WO | WO2004007329 A1 | 1/2004 |
| WO | WO2005075163 A1 | 8/2005 |
| WO | WO2006038946 A1 | 4/2006 |
| WO | WO2007029115 A1 | 3/2007 |
| WO | WO2007039800 A1 | 4/2007 |
| WO | WO2007126347 A1 | 11/2007 |
| WO | WO2008001209 A2 | 1/2008 |
| WO | WO2008015594 A2 | 2/2008 |
| WO | WO2008037281 A1 | 4/2008 |
| WO | WO2008123348 A1 | 10/2008 |
| WO | 2008155618 A2 | 12/2008 |
| WO | WO2009065497 A1 | 5/2009 |
| WO | WO2009065500 A1 | 5/2009 |
| WO | WO2010028786 A1 | 3/2010 |
| WO | WO2011001773 A1 | 1/2011 |
| WO | WO2011101773 A1 | 8/2011 |
| WO | 2015079367 A1 | 6/2015 |
| WO | 2018037304 A1 | 3/2018 |

OTHER PUBLICATIONS

USPTO Ofice Action dated Jul. 26, 2010, regarding U.S. Appl. No. 12/070,879, 14 pages.
USPTO Notice of Allowance dated Mar. 9, 2011, regarding U.S. Appl. No. 12/070,879, 7 pages.
International Search Report dated Jan. 24, 2013 regarding EP Application No. 12167184.6, 5 pages.
International Search Report dated Jan. 24, 2013 regarding EP Application No. 12167183.8, 8 pages.
International Search Report dated Aug. 8, 2013 regarding EP Application No. 13166330.4, 7 pages.
International Search Report dated Aug. 16, 2013 regarding EP Application No. 13166314.8, 6 pages.
"Reciprocating Mechanisms", Franklin Jones, vol. 1, date unknown, 2 pages.
International Search Report pertaining to PCT/US2016/033288, dated Aug. 18, 2016, 7 pages.
Reciprocating Mechanisms, Ingenious Mechanisms for Designers and Inventors, Franklin Jones vol. 1.

* cited by examiner

CONFIGURABLE SINGLE TRANSFER INSERT PLACEMENT METHOD AND APPARATUS

BACKGROUND OF THE INVENTION

Embodiments of the invention relate to a method and apparatus for receiving and cutting a continuous web, and transferring articles, or inserts, such as absorbent pads cut from the web in the manufacture of disposable absorbent articles such as diapers, incontinence control garments or female sanitary pads as they advance along a production line. More particularly, embodiments of the invention relate to such a method and apparatus being configurable, so as to provide for adjustments in operation of the method and apparatus in an efficient manner and therefore accommodate cutting and transferring of articles of differing types and sizes.

In the production and manufacture of disposable products such as sanitary napkins or pants-type diapers, it frequently becomes necessary to manufacture a component of the product in one orientation, and then to spin that component part to a predetermined angle, which is suitably oriented for use in another step in the production process. As an example, a typical article or web to be reoriented is an absorbent pad. Existing apparatuses function to receive a continuous web onto a transfer mechanism prior to cutting the web into discrete pads, cut a section from the web thereby forming a pad, spin the pad to a predetermined angle, and transfer the pad for placement on a receiving surface. Additionally, the apparatus may also function to control a velocity and pitch between cut pads to achieve a desired placement pitch on the receiving surface. In the case of a diaper, for example, the pad may be an absorbent insert to be placed on a fluid impervious chassis. Therefore, the web may be cut at a cut pitch, X, and the receiving pitch, or distance between consecutive chasses at the receiving surface may be represented as Y, where Y is comprised of a chassis trailing edge, an interval space, and a subsequent chassis leading edge.

With regard to the transfer device that is used to rotate and re-pitch the pads for placement on the receiving surface, the transfer device is generally constructed to include a large wheel having a plurality of rotating pucks secured thereto that are selectively operable to provide the rotating and re-pitching of the pads. The wheel is driven and supported by a shaft extending from the drive side of the machine, with the pucks in turn being rotated along with the wheel. Additionally, each of the pucks functions to spin/turn about its own spin axis, so as to provide for turning (e.g., 90 degree turn) of the pads.

While existing transfer devices perform adequately for rotating and re-pitching pads for placement on a receiving surface, it is recognized that existing transfer devices have several limitations or drawbacks. Primarily, existing transfer devices are considered to be "non-configurable" in that the number of pucks provided on the system is defined—with the selective addition/removal of pucks to accommodate different process flows and/or product types not being possible. Accordingly, in order to implement a different process flow or accommodate a different product type that requires a transfer device with a different number of pucks from a transfer device currently in use, it is necessary to swap out the entire transfer device. Such a swapping out of the transfer devices is a difficult process, as the transfer device are heavy units (i.e., thousands of pounds) that require specialized equipment for moving, and may also be a time-consuming process that increases downtime of the device.

Therefore, it is desirable to provide a transfer device (and overall cutting/transferring apparatus) that is configurable, so as to accommodate the cutting and transferring of articles of differing types and sizes. Such a device/system would provide for the selective addition/removal of pucks, as well as configuring of an anvil and knife for cutting a continuous web into discrete articles/pads to be carried on the transfer device.

BRIEF DESCRIPTION OF THE INVENTION

In accordance with one aspect of the invention, a configurable cutting and transfer apparatus includes a cutter mechanism configured to cut an incoming web of material into a plurality of discrete articles and a transfer mechanism operable with the cutter mechanism to transfer and rotate the plurality of discrete articles from at least a web receiving location to an article placement location. The transfer mechanism further includes a drive shaft rotatable about a transfer axis, a carriage plate mounted to the drive shaft so as to rotate therewith about the transfer axis, and a segmented puck wheel comprising a plurality of carriage units securable to, and repositionable on, the carriage plate so as to rotate therewith to travel along a transfer path about the transfer axis from at least the web receiving location to the pad placement location, each of the plurality of carriage units including a puck that is selectively operable to provide a rotating and re-pitching of the articles between the web receiving location and the pad placement location.

In accordance with another aspect of the invention, a method for configuring a configurable cutting and transfer apparatus includes providing a cutter mechanism configured to cut an incoming web of material into a plurality of discrete articles and providing a transfer mechanism operable with the cutter mechanism to transfer and rotate the plurality of discrete articles from at least a web receiving location to an article placement location. Providing the transfer mechanism further includes providing a drive shaft having a carriage plate mounted thereto, the drive shaft and carriage plate rotatable about a transfer axis and mounting a plurality of carriage units to the carriage plate to form a segmented puck wheel, the plurality of carriage units rotatable with the carriage plate to travel along a transfer path about the transfer axis from at least the web receiving location to the pad placement location, with each of the plurality of carriage units including a puck operable to provide a rotating and re-pitching of the articles between the web receiving location and the pad placement location. A construction of the carriage plate and the plurality of carriage units enables mounting of the plurality of carriage units in a plurality of arrangements and in various numbers on the carriage plate, so as to provide a configurable cutting and transfer apparatus.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the invention are directed to a configurable cutting and transfer apparatus and method of operating and assembling thereof. Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Figure 1:
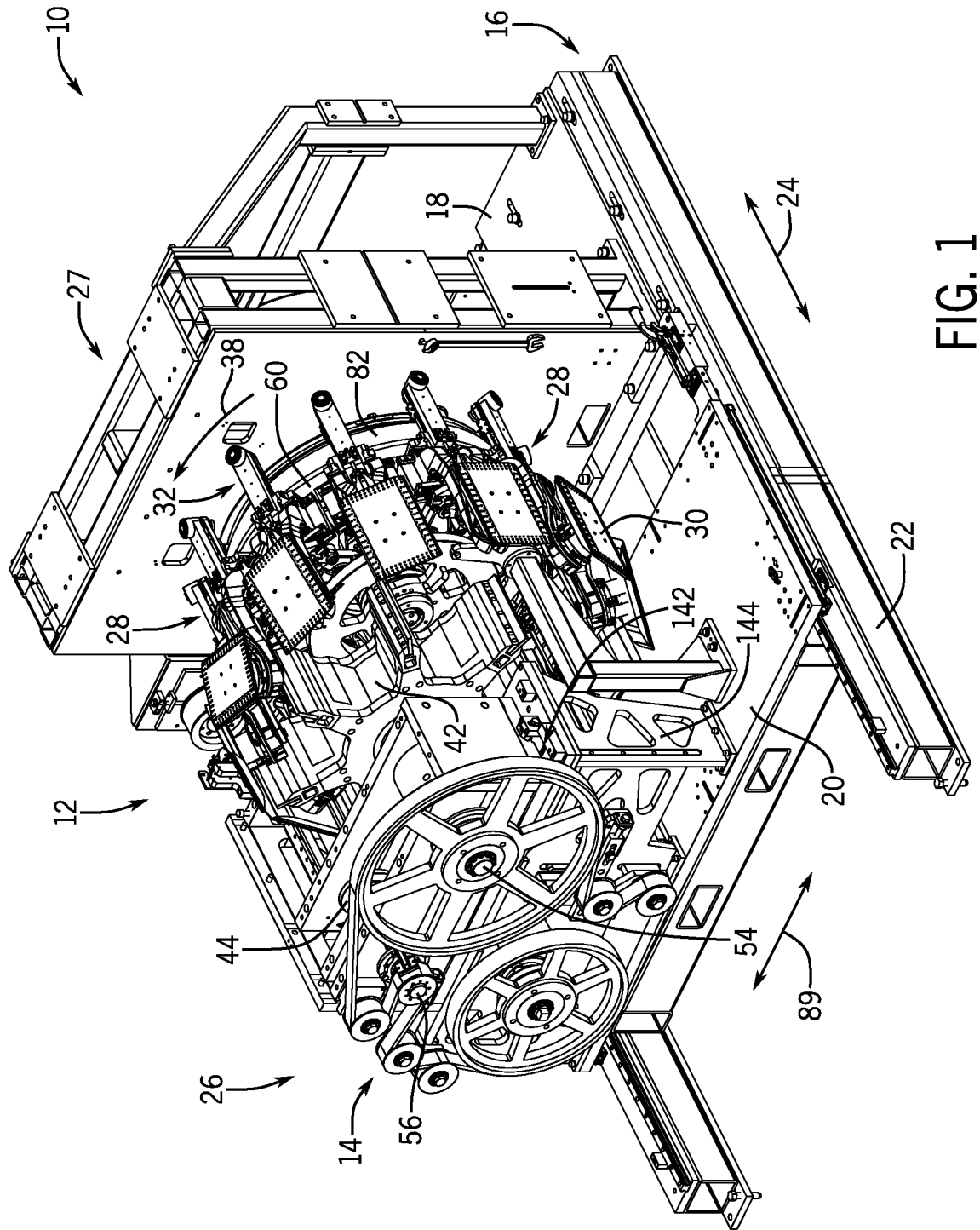
FIG. 1 is a front perspective view of a configurable cutting and transfer apparatus, according to an embodiment of the invention.
Figure 2:
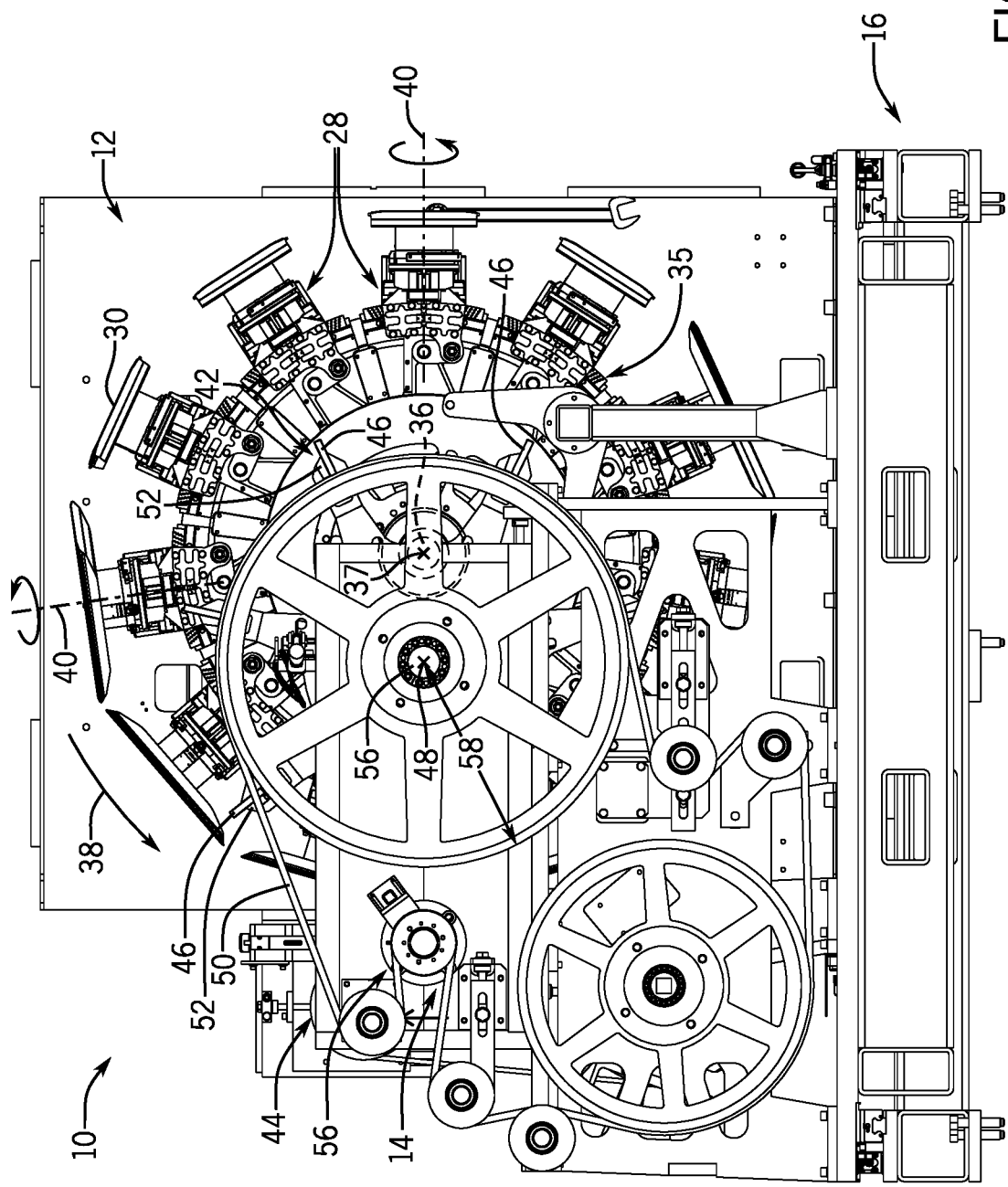
FIG. 2 is a front elevation view of the apparatus of FIG. 1.
Figure 3:
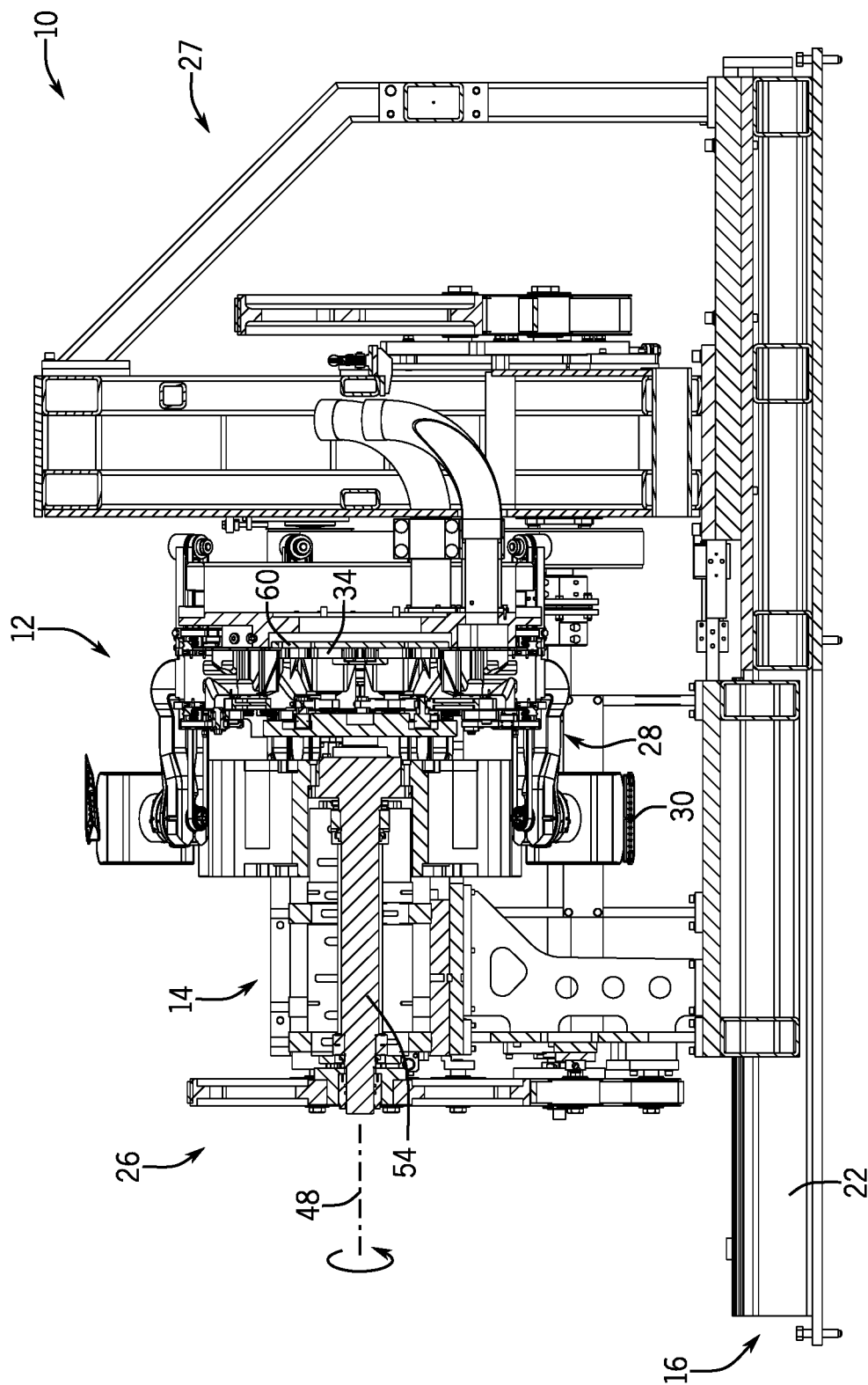
FIG. 3 is a right-side cross-sectional view of the apparatus of FIG. 1 taken along line 1-1.

Referring to FIGS. 1-3, front perspective, front elevation, and right-side cross-sectional views of a configurable cutting and transfer apparatus 10 (or "apparatus 10") are shown, respectively, according to an exemplary embodiment of the invention. The apparatus 10 preferably includes a transfer mechanism 12 and a cutter mechanism 14, each of which may be mounted on a base frame 16 via a respective floor plate 18, 20—with transfer mechanism 12 mounted to plate 18 and cutter mechanism 14 mounted to plate 20. Base frame 16 comprises a pair of rails 22 on which floor plates 18, 20 are mounted and, in a preferred embodiment, one or more of floor plates 18, 20 may linearly translate along rails 22 in a direction 24 so as to provide for movement of the transfer mechanism 12 and/or cutter mechanism 14 along rails 22. As will be explained in greater detail below, when it is desirable to reconfigure the cutting and transfer apparatus 10 in order to implement a different process flow and/or accommodate a different product type, cutter mechanism 14 and/or transfer mechanism 12 may be moved along rails 22 of frame 16 to space the mechanisms apart and thereby provide easier access to components of the apparatus 10 from an operator side 26 of the apparatus (opposite from a drive side 27) and to enable the selective removal and addition of components in order to reconfigure the apparatus 10.

As shown in FIGS. 1-3, the transfer mechanism 12 includes a plurality of carriage units 28 that are selectively addable and removable from the transfer mechanism 12, with each carriage unit 28 including a puck 30 that may be engaged and disengaged from a puck support 32 of the carriage unit 28. The carriage units 28 are coupled to a carriage plate 34 of the transfer mechanism 12 to collectively form a segmented puck wheel 35—with the term "segmented" understood to refer to the fact that the puck wheel 35 is not a unitary member but is formed from a plurality of individual/modular carriage units 28 that are selectively addable and removable from the carriage plate 34 to form a puck wheel 35 of a desired configuration. The carriage plate 34 is fixedly coupled to a motor-driven shaft 36 that provides a substantially operationally constant rotational force to the carriage plate 34, with a motor (not shown) that drives the shaft 36 also driving all other movement in the apparatus 10 (i.e., all movers in transfer mechanism 12 and cutter mechanism 14). The carriage plate 34—along with carriage units 28 and pucks 30 of puck wheel 35 mounted thereto—is thus caused to rotate about a puck transfer axis 37 that is a major axis of rotation, so as to move the pucks about a transfer path 38. As used throughout the description of the preferred embodiment, "rotate" and its variants refer to the movement of an entire puck 30 (and carriage unit 28) about the transfer axis 37, while "spin" and its variants refer to the radial spin of a puck 30 about a puck spin axis 40, which is substantially perpendicular to the puck transfer axis 37.

The cutter mechanism 14 preferably comprises an anvil wheel 42 (or "anvil ring") and a knife roll 44 that interact with one another to cut discrete pads or inserts from a continuous web that is provided to the cutting and transfer apparatus 10. The anvil wheel 42 includes a plurality of anvils 46 radially disposed about an anvil wheel axis 48, while the knife roll 44 includes one or more knife blades 50 thereon. According to one embodiment, the anvils 46 comprise carbide inserts held in place with a wedge block 52 (secured with socket head cap screws). To ensure the knife blade 50 cuts successfully on an anvil 46 of the anvil wheel 42, the anvils 46 must be equal in height. While cutter mechanism 14 is described herein as comprising an anvil wheel 42 and knife roll 44, it is recognized that these components could be reversed—with a knife wheel and anvil roll being utilized as compared to the illustrated embodiment. Operation of the knife wheel and anvil roll would be substantially similar to the operation of the anvil wheel 42 and knife roll 44 that is set forth here below.

Each of the anvil wheel 42 and knife roll 44 is coupled to a respective drive shaft 54, 56 that causes rotation thereof. In operation, the apparatus 10 receives a continuous web 146 from a source and the web is brought into contact with a puck 30. One of anvils 46 is then caused to rotate into position so as to be aligned with knife blade 50 and cooperate therewith (i.e., come into contact with) to cut the web proximate a leading edge of the puck 30. After receipt of the web 146 and the cut made near the leading edge, the puck 30 proceeds to travel along the transfer path 38 and past the knife roll 44, at which point the next anvil 46 on anvil wheel 42 rotates into position to cooperate with knife blade 50 to cut the web proximate the trailing edge of the puck 30 to cut a section from the web that comprises an insert or pad. The section is held to the puck 30 by a vacuum and caused to rotate about the transfer path 38, as will be explained in greater detail later on.

In an exemplary embodiment, the anvil wheel 42 preferably has fewer anvils 46 than the number of pucks 30 provided on the transfer mechanism 12. The fewer number of anvils 46 provided allows a greater offset 58 between the anvil wheel axis 48 and the puck transfer axis 37. The eccentric offset 58 causes a virtual withdrawal of the anvils 46 to allow more space to achieve desired pitch change between the pucks 30.

Figure 4:
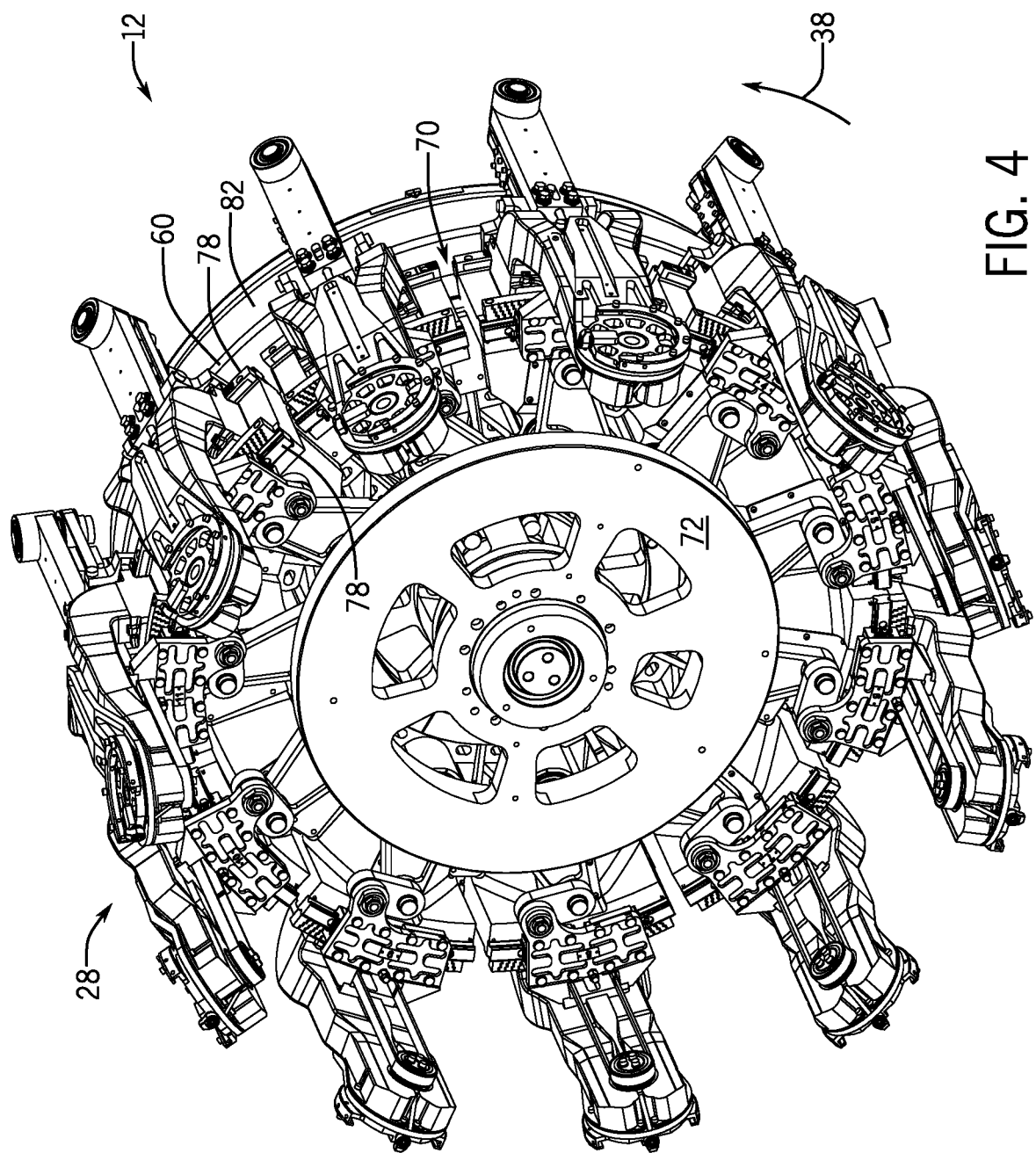
FIG. 4 is a perspective view of a transfer mechanism included in the apparatus of FIG. 1, according to an embodiment of the invention.
Figure 5:
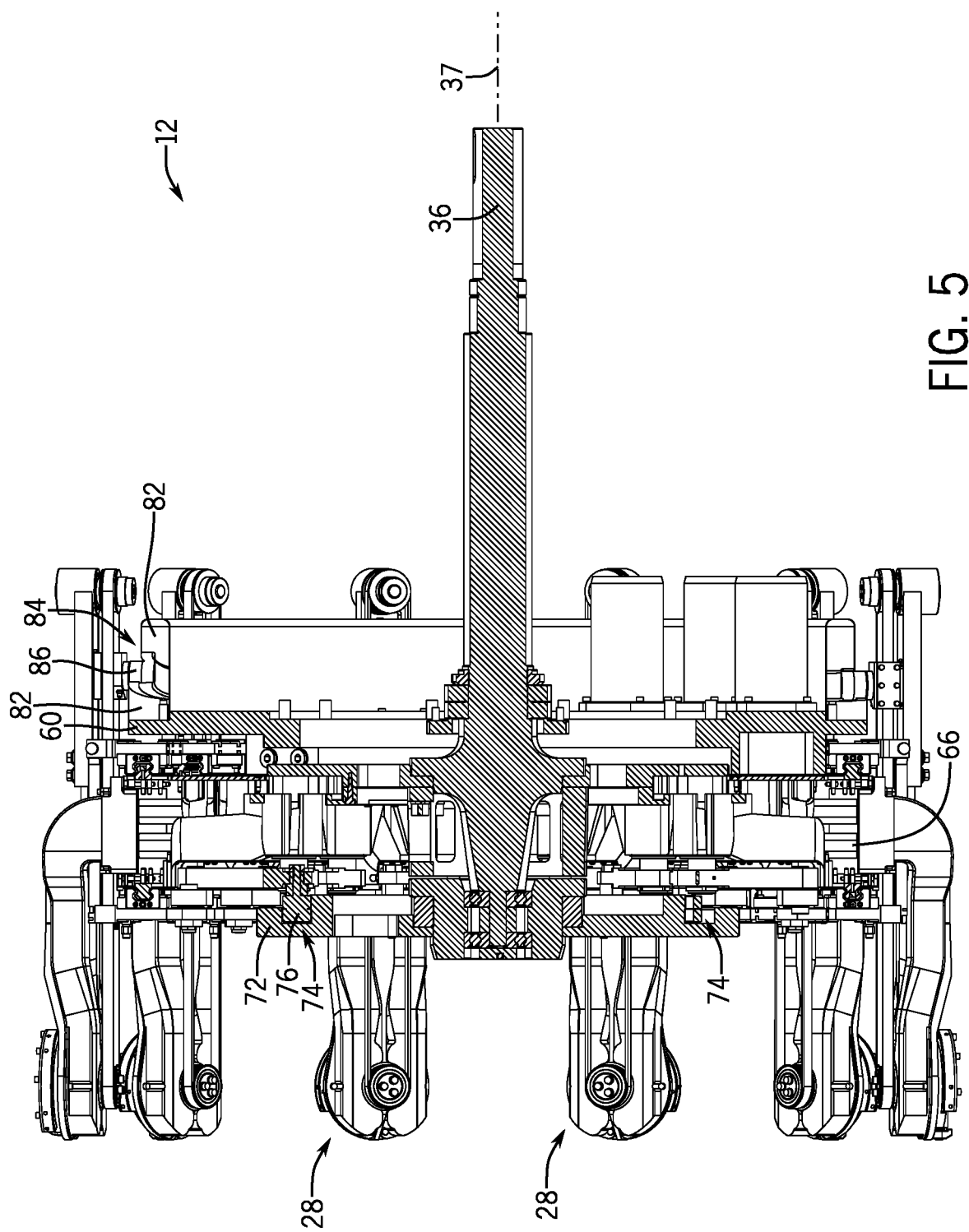
FIG. 5 is a right-side cross-sectional view of the transfer mechanism of FIG. 4 taken along line 4-4.
Figure 6:
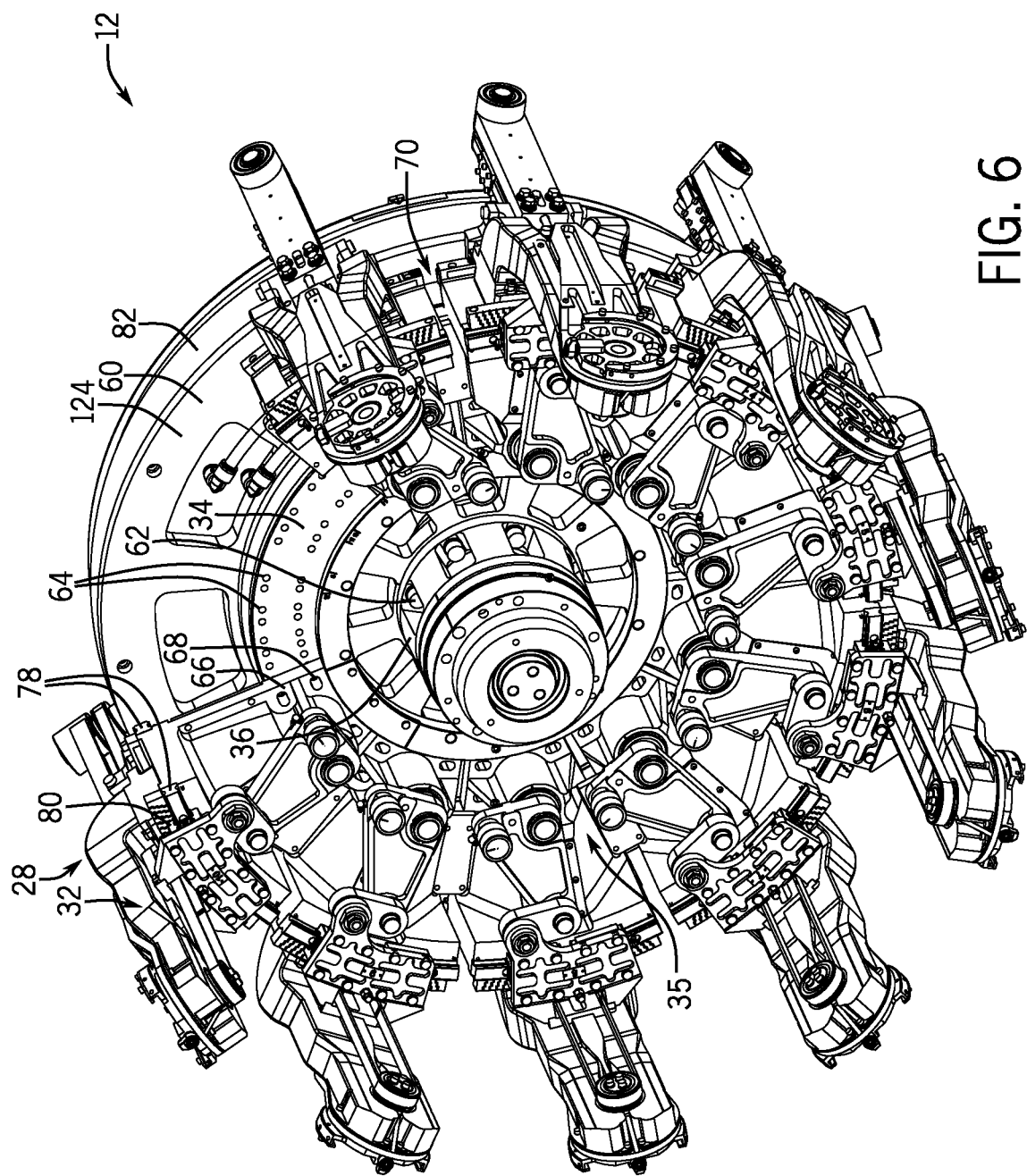
FIG. 6 is a perspective view of the transfer mechanism of FIG. 4 with a face cam plate and a number of carriage units removed therefrom.

Referring still to FIGS. 1-3 and now also to FIGS. 4-6, the transfer mechanism 12 is shown in greater detail for purposes of better describing the structure and operation thereof. As indicated above, transfer mechanism 12 includes a carriage plate 34 that is fixedly coupled to and driven by a drive shaft 36, so as to rotate about puck transfer axis 37. Carriage plate 34 is positioned on an operator side of a stationary base plate 60 to provide a surface for coupling the carriage units 28 thereto. According to an embodiment, carriage plate 34 includes fastener holes 62 formed therethrough for securing the carriage plate 34 to the shaft 36 and fastener holes 64 formed therethrough for coupling the carriage units 28 to the carriage plate 34, with the fastener holes 64 arranged as two concentric rings/circles on the carriage plate 34. The number/arrangement of fastener holes 64 is such that carriage plate 34 may receive any of a number of different carriage units 28 thereon at differing locations and at different spacings, with it being recognized that each carriage unit 28 included in transfer mechanism 12 would be secured to carriage plate 34 via at least four fasteners.

In mounting carriage units 28 to carriage plate 34, a mounting block 66 of a respective carriage unit 28 is positioned on carriage plate 34 such that fastener holes 68 in mounting block 66 align with fastener holes 64 on carriage plate 34. Fasteners are then inserted through the fastener holes 64, 68 in mounting block 66 and carriage plate 34 to secure the carriage unit 28 to the carriage plate 34. Depending on the number of carriage units 28 mounted to carriage plate 34, it is recognized that gaps 70 may be present between adjacent carriage units 28, such as shown in the present embodiment where eleven carriage units 28 are included in transfer mechanism 12. These gaps 70 between adjacent carriage units 28 may be left open or, according to one embodiment, may be filled with spacers (not shown) that fits in the gaps 70 and are secured to carriage plate 34.

To facilitate position modification of the pucks 30, the transfer mechanism 12 also includes a face cam plate 72 situated about the transfer axis 37 and positioned on the operator side 26 of the carriage plate 34. The face cam plate 72 is positioned apart from the carriage plate 34 by a distance that provides for attachment of the carriage units 28 to the carriage plate 34. The face cam plate 72 is preferably a stationary plate having a pitch cam race 74 therein or thereon, with the pitch cam race 74 formed on a side of face cam plate 72 facing drive side 27. The face cam plate 72 assists the pitch change, or altered circumferential spacing of pucks 30. Although different designs could be employed, where the pitch cam race 74 is situated further from the puck transfer axis 37, the velocity of the puck 30 will be higher than where the pitch cam race 74 is positioned nearer the transfer axis 37. As described in this preferred embodiment, the maximum pitch change, therefore, is generally determined by the shape of the pitch cam race 74. The pitch change is accomplished by using a pitch cam follower 76 on each respective carriage unit 28, which is preferably a roller bearing, in sliding or rolling communication with the pitch cam race 74. Located preferably near a radial distal edge of each respective carriage unit 28 is a pair of pitch rails 78 affixed to mounting block 66, which allow controlled circumferential displacement of the pucks 30. The puck support 32 is provided with rail guides 80, which are slidably disposed on the pair of pitch rails 78.

To facilitate spinning or turning of the pucks 30, the transfer mechanism 12 also includes a barrel cam 82 situated about the transfer axis 37 and positioned on the drive side of the base plate 60. The barrel cam 82 is preferably a stationary ring-shaped member having a spin cam race 84 provided around an outside edge/surface thereof. To achieve desired spin of the pucks 30, a spin cam follower 86 of carriage unit 28, which is preferably a roller bearing, is in sliding or rolling communication with the spin cam race 84. In one embodiment, spin cam race 84 is configured to provide a ninety-degree puck rotation, but it is recognized that configuration of the spin cam race 84 is generally determined by the desired spin angle of the puck 30.

Referring still to FIGS. 4-6 and now also to FIGS. 7-10, a carriage unit 28 is shown in greater detail for purposes of better describing the structure and operation thereof. As indicated above, carriage unit 28 includes a mounting block 66 and a puck support 32 that is positioned on mounting block 66. Mounting block 66 includes fastener holes 68 formed generally in a bottom portion thereof for securing carriage unit 28 to the carriage plate 34. A pair of pitch rails 78 is secured onto a top surface of mounting block 66 (i.e., a radially outward facing surface when bolted to carriage plate 34) via rail fasteners 88, with the pitch rails 78 running parallel to a machine direction 89 in which transfer mechanism 12 rotates. The pitch rails 78 have a generally arcuate shape mirroring that of the top surface of mounting block 66, such that when a plurality of carriage units 28 are secured about carriage plate 34, a generally circular profile is formed by the top surfaces of the mounting blocks 66.

Figure 7:
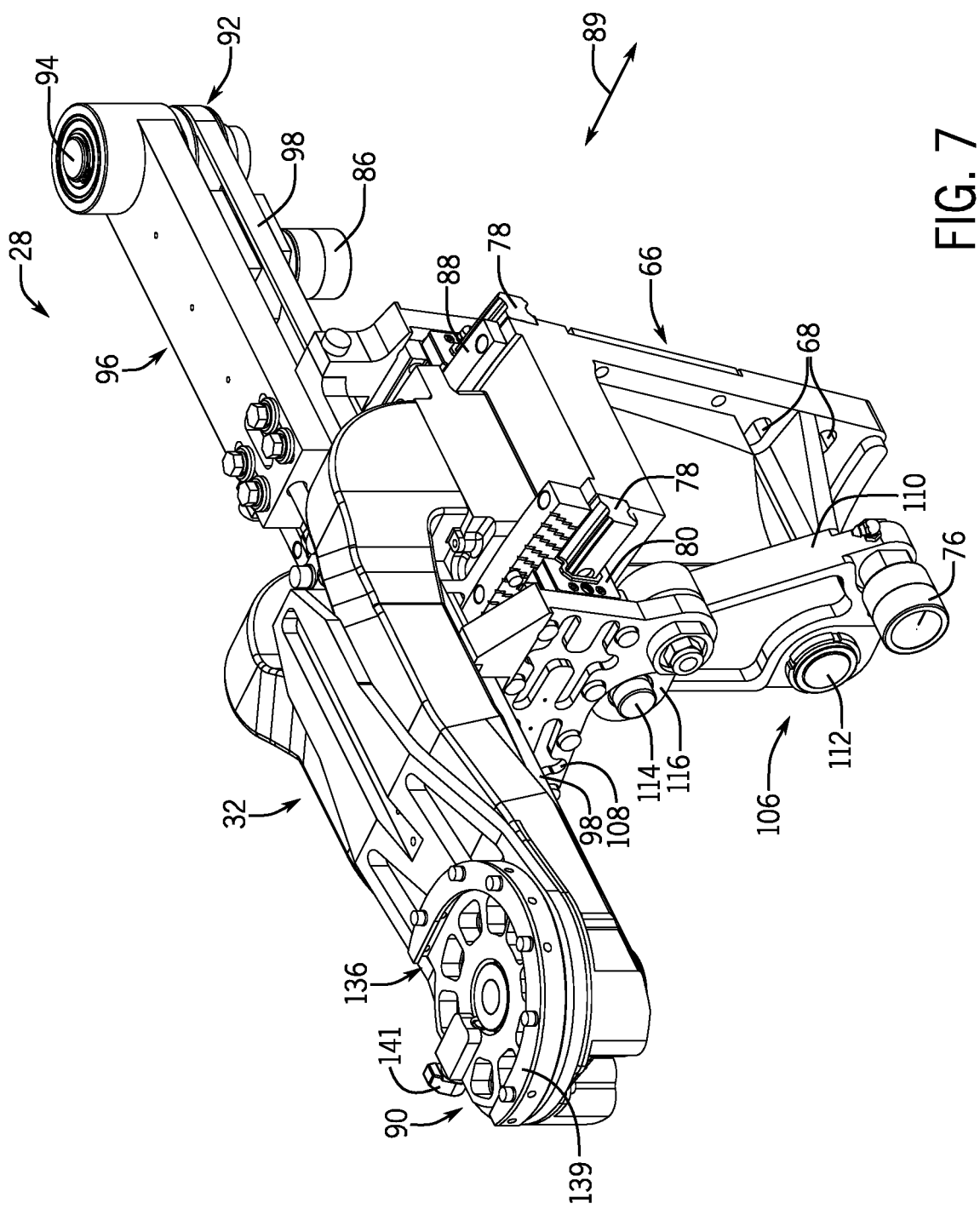
FIG. 7 is a front perspective view of a carriage unit included in the apparatus of FIG. 1, according to an embodiment of the invention.
Figure 8:
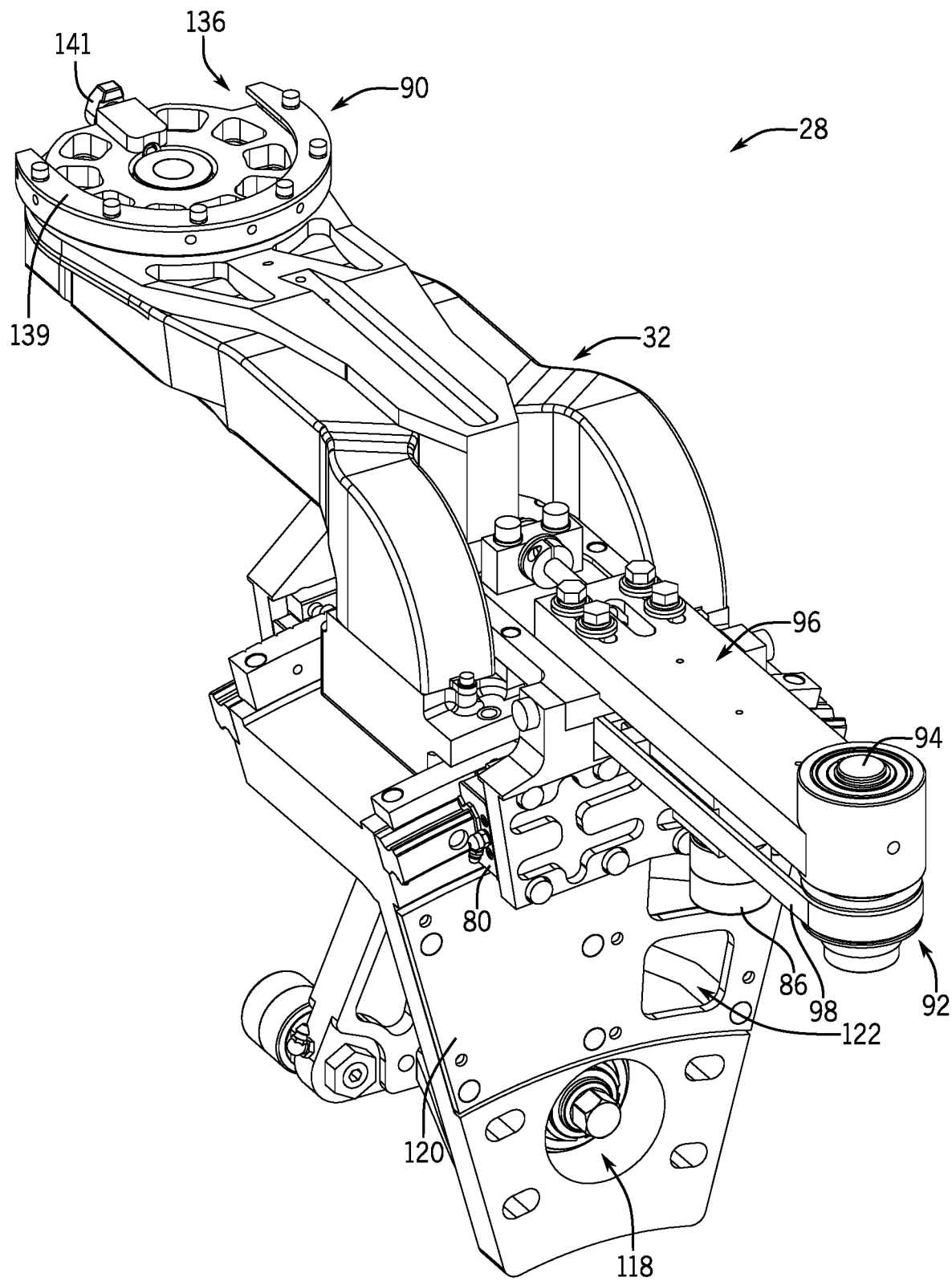
FIG. 8 is a rear perspective view of the carriage unit of FIG. 7.

As best shown in FIGS. 7 and 8, the puck support 32 is secured on mounting block 66 via the mating of rail guides 80 of the puck support 32 with pitch rails 78. The puck support 32 is oriented generally orthogonal to the pitch rails 78 with a puck mount 90 provided on one end of puck support 32 (i.e., on operator side 26 of apparatus 10) and an idler side pully or sprocket 92 provided on the opposite end of puck support 32 and mounted on an idler shaft 94. The rail guides 80 are slidably disposed on the pair of pitch rails 78, such that puck support 32 may translate thereon in a direction parallel to the machine direction 89 in which transfer mechanism 12 rotates, thereby allowing the position/velocity of the puck support 32 (and puck 30) to be altered as compared to the puck support 32 of other carriage units 28. Puck support 32 further comprises a take up frame 96 extending outwardly from an area adjacent rail guides 80 to the idler side pully 92, with a belt 98 provided on an underside of the take up frame 96. The belt 98 extends generally a length of the puck support 32 from the idler side pully 92 to a puck side pully 100 (FIG. 9) that is located beneath puck mount 90 and on a pad turner shaft 102. The belt 98 is driven by interaction thereof with spin cam follower 86, which is contained within a spin cam follower holder 104 (FIG. 9) positioned beneath take up frame 96. As spin cam follower 86 interacts with spin cam race 84 and rotates therein, the rotation of the follower spin cam follower 86 is translated to belt 98, which in turn causes rotation of puck side pully 100 and pad turner shaft 102 so as to cause rotation of the puck mount 90 and a puck 30 secured thereto.

Also included in carriage unit 28 is a triadic linkage system 106 that functions to transfer the tracking of the pitch cam follower 76 to the carriage module 28 (i.e., to puck support 32 and puck 30) and a puck holder plate 108 that aids in securing the triadic linkage system 106 to the puck support 32. As shown in FIGS. 7-10, triadic linkage system 106 includes a triangularly shaped link member 110 having a number of openings 111 therein—with the openings 111 receiving pitch cam follower 76 and a pivot shaft 112 therein, as well as a pin 114 that secures a connecting link 116 of the triadic linkage system 106 to the link member 110. The pitch cam follower 76 is secured within one opening 111 of link member 110, while pivot shaft 112 extends through another opening 111 and into a receptacle 118 formed in a bottom portion of mounting block 66, so as to enable rotation/pivoting of the link member 110 relative to the mounting block 66. The connecting link 116 is secured to link member 110 on one end thereof via pin 114 and is secured on the other end thereof to puck holder plate 108—with puck holder plate 108 in turn secured to one of rail guides 80. In operation, translation of pitch cam follower 76 within the pitch cam race 74 causes rotation of link member 110 about pivot shaft 112, which in turn imparts movement/rotation to connecting link 116 so as to cause rail guides 80 of puck support 32 to translate along pitch rails 78. Accordingly, movement of the puck support 32 and associated puck 30 is generated in the machine direction 89 so as to increase/decrease a distance between said puck 30 and the pucks 30 of adjacent carriage units 28 at a controlled velocity.

Figure 9:
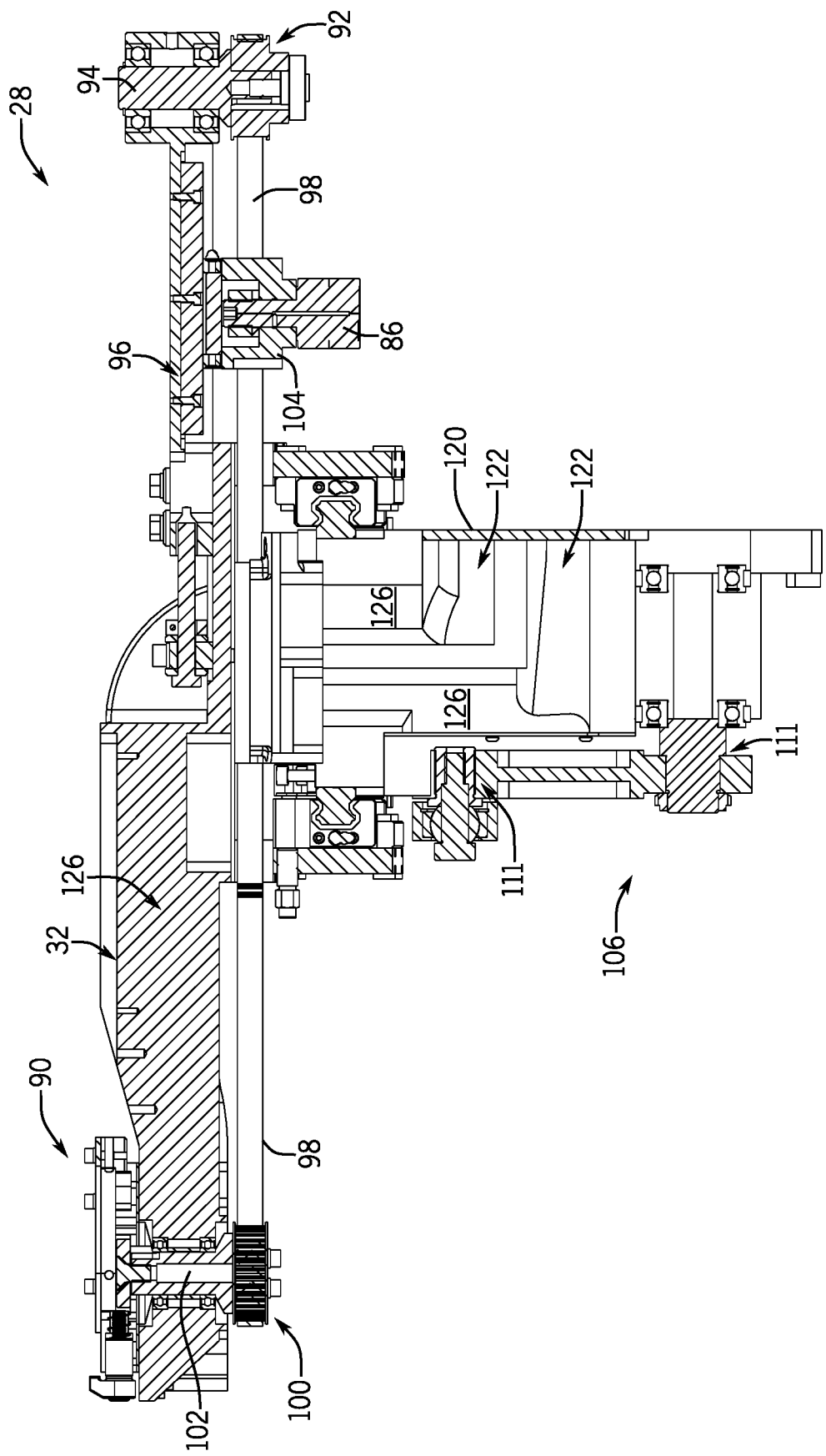
FIG. 9 is a right-side cross-sectional view of the carriage unit of FIG. 7 taken along line 7-7.
Figure 10:
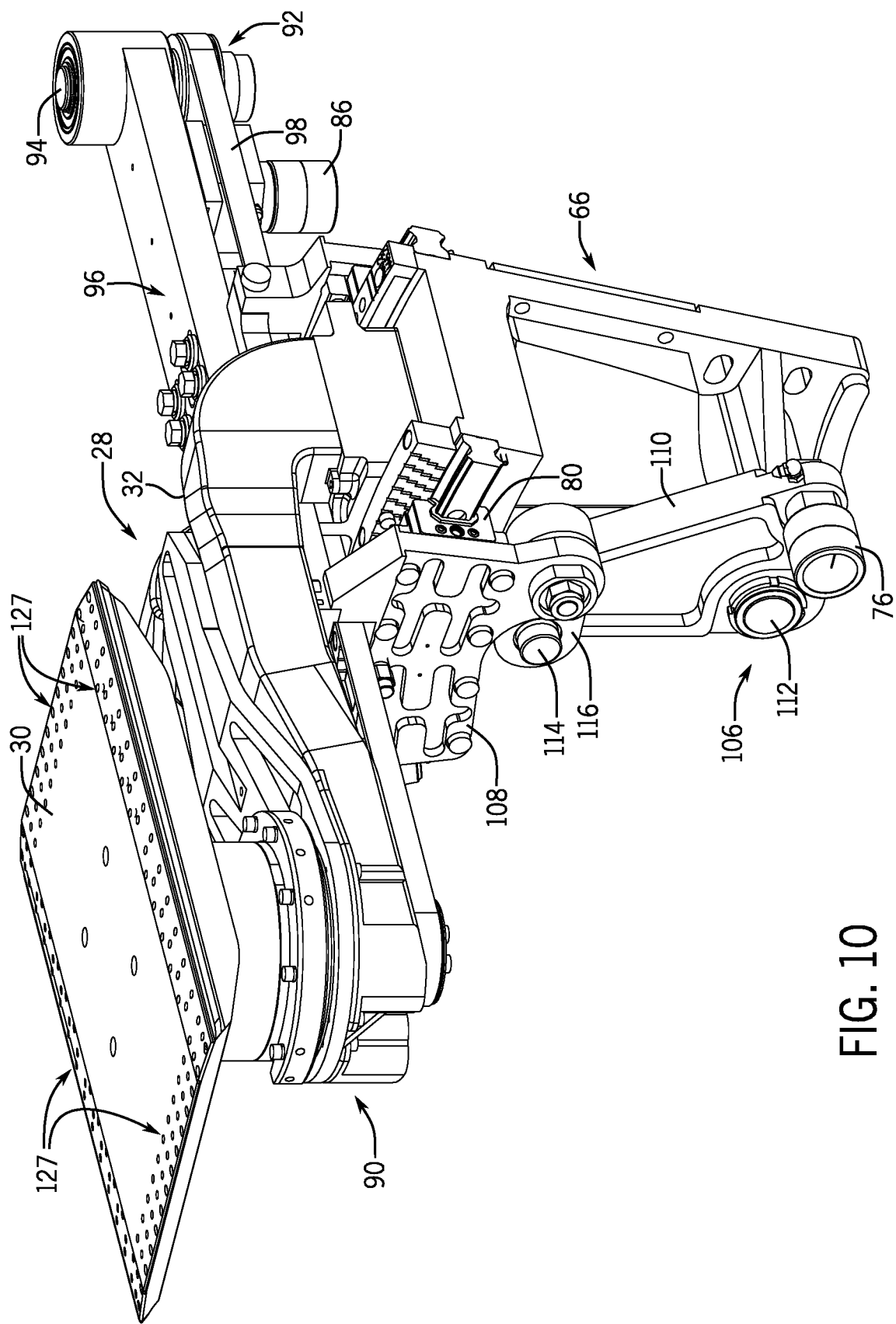
FIG. 10 is a front perspective view of the carriage unit of FIG. 7 with a puck mounted to the puck support thereof.

Also included in carriage unit 28 are a number of components that enable communication of a vacuum from a vacuum source (not shown) of apparatus 10 to the puck 30. As shown in FIGS. 8 and 9, a vacuum plate 120 is secured to mounting block 66 on a back surface thereof in an area above fastener holes 68. The vacuum plate 120 includes one or more openings 122 formed therein that provide an air passage into/out from the puck support 32 to enable communication of a vacuum to the puck 30. When mounting block 66 is fastened to carriage plate 34, the opening(s) 122 are aligned with openings 124 in the base plate 60 (FIG. 6), such that the vacuum source is fluidly connected to the carriage unit 28. The openings 122 in vacuum plate 120 are fluidly coupled with vacuum passages 126 formed in puck support 32, with the vacuum passages 126 extending through the puck support 32 out to the puck mount 90 such that a vacuum is commutable therethrough. A vacuum is drawn through the vacuum passages 126 and is divided into multiple vacuum zones 127 at the puck 30 (FIG. 10), with the orientation of the puck 30 to the various zones 127 controlling whether the pucks 30 will pick-up or transfer (i.e., activate/deactivate the vacuum through the puck 30). According to one embodiment, each vacuum puck 30 has four vacuum zones 127 to assist in holding the pad/insert during pick-up and transfer. As the pucks 30 rotate, the leading and trailing vacuum zones 127 change. Pucks rotate 90 degrees after pick-up and then drop off the pad/insert to a receiving surface (not shown), such as a vacuum transfer roll.

Figure 11:
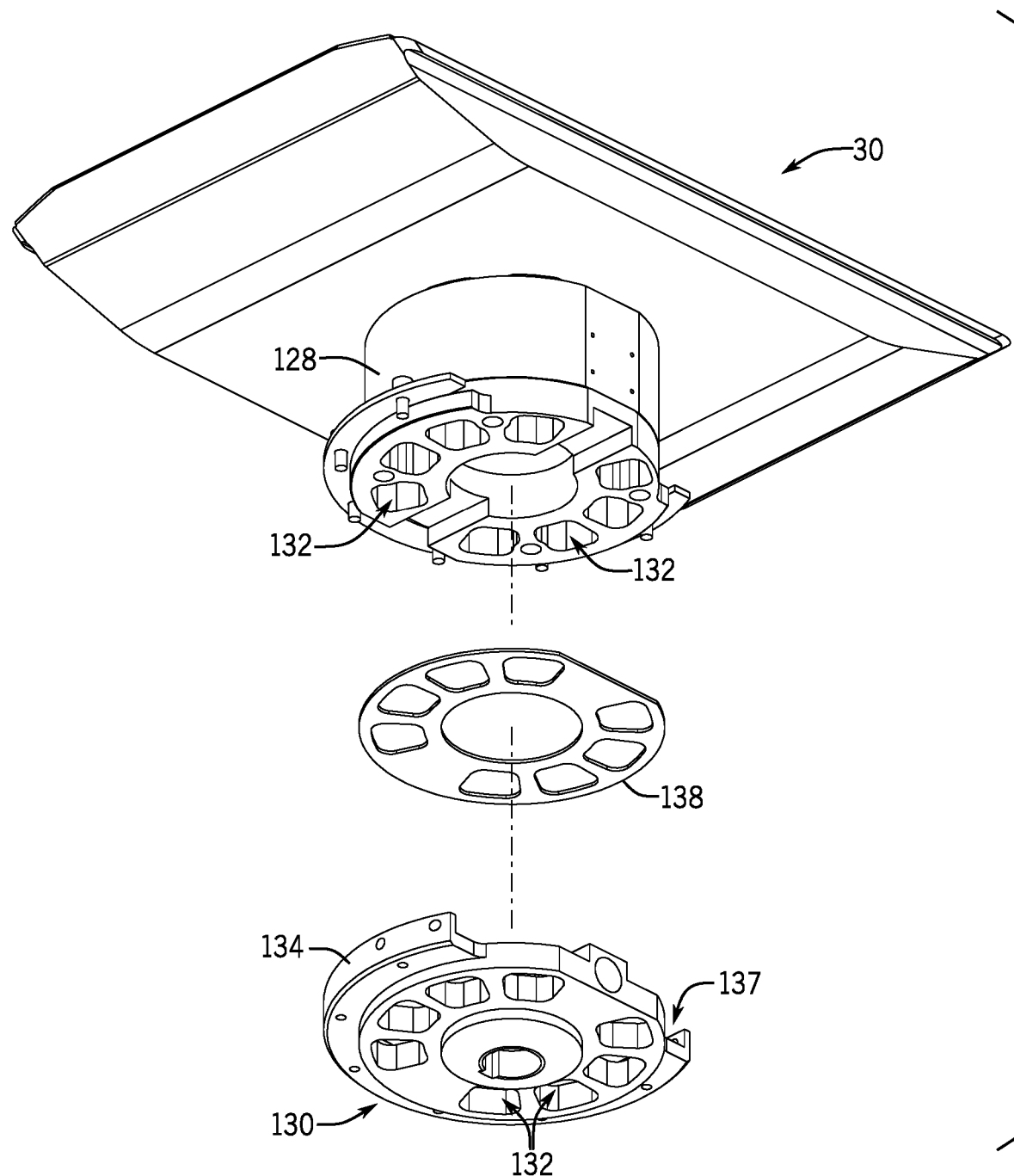
FIG. 11 is a bottom perspective view of the puck of FIG. 10, according to an embodiment of the invention.

Referring now to FIG. 11, an underside of a puck 30 is shown in greater detail for purposes of better describing the mounting thereof to the puck mount 90 of carriage unit 28. The underside of puck 30 includes an upper assembly 128 and a puck connector 130. Each of the upper assembly 128 and puck connector 130 include an arrangement of openings 132 therein that provide for a vacuum to be communicated to puck 30 via puck support 32, with communication of the vacuum to the puck 30 from puck support 32 as being described above. Puck connector 130 is configured to engage puck mount 90 according to a "quick connector" type engagement, e.g., a "hitch and receiver" type engagement. In the illustrated example, a flange 134 on puck connector 130 slidingly engages with a lipped recess 136 (FIGS. 7 and 8) of puck mount 90 to secure the puck 30 to the puck support 32, with a slot 137 formed in the flange 134 that engages a protrusion 139 on the puck mount 90 and a tab 141 that may snap the puck connector 130 into place on the puck mount 90 (FIGS. 7 and 8). The structure of puck connector 130 and mating thereof with puck mount 90 allows for pucks 30 to be easily swapped out and exchanged on carriage unit 28 based on the specific set-up of transfer mechanism 12. Different size pucks 30 can be connected to carriage units 28 to accommodate the cutting and transferring of articles of differing types and sizes.

Figure 17:
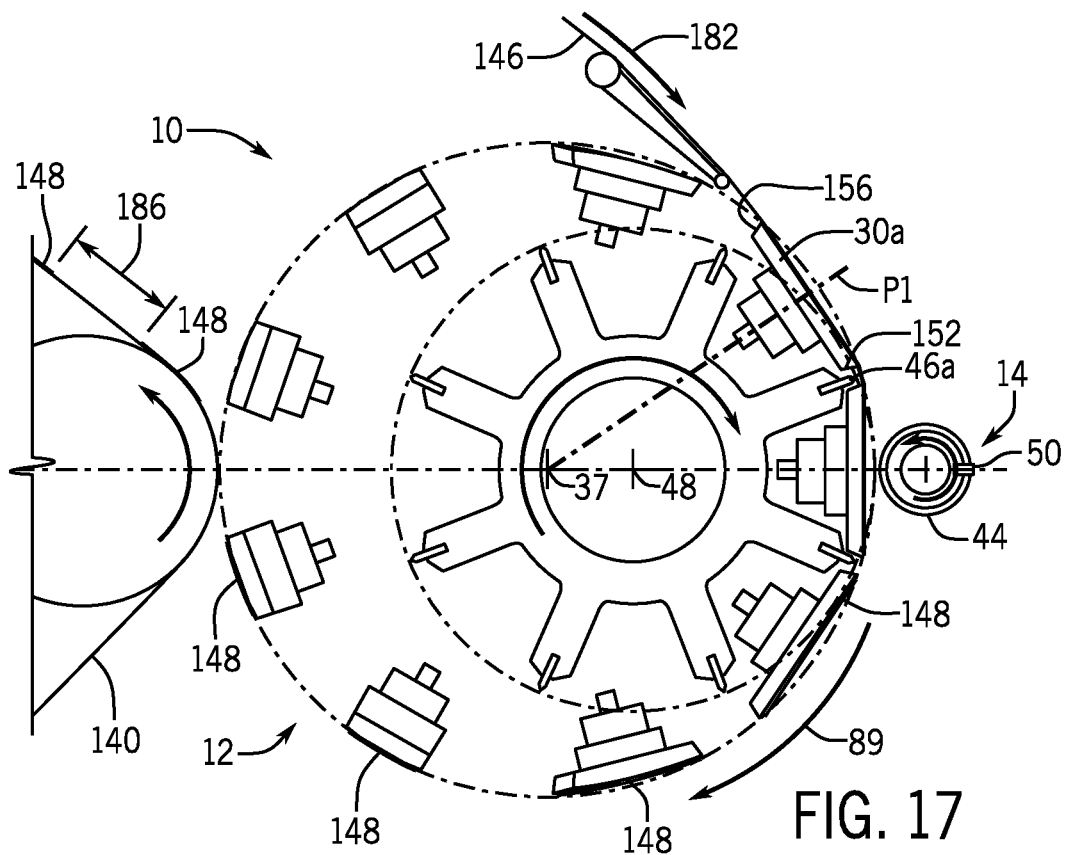
FIG. 17 is a simplified front elevation view of a configurable cutting and transfer apparatus in a first position, according to an embodiment of the invention.

As further shown in FIG. 11, one or more shim spacers 138 may be positioned between upper assembly 128 and puck connector 130 in order to selectively adjust a height that puck 30 extends out from puck support 32, and thereby increase a vertical positioning or offset of the puck 30 relative to the transfer axis 37. That is, in the interaction of transfer mechanism 12 with a receiving surface 140 (e.g., vacuum transfer roll, such as shown in FIG. 17) to which rotated pads/inserts are deposited on, it is recognized that a proper spacing or gap between the pucks 30 and the receiving surface 140 is desired at a drop-off location where the pads/inserts are deposited from the pucks 30 onto the receiving surface 140, in order that the receiving surface 140 is close enough to the article carried by puck 30 such that a vacuum on the receiving surface 140 is able to attract the article thereto. In order to control the size of this gap, a shim spacer 138 having a desired thickness may be positioned between the upper assembly 128 and puck connector 130—with shim spacers 138 of 0.005 inch (0.127 mm), 0.010 inch (0.256 mm), 0.015 inch (0.381 mm), 0.020 inch (0.508 mm), and 0.025 inch (0.635 mm) being available, for example, in order to selectively control the gap size. It is also recognized that multiple shim spacers 138 could be stacked between the upper assembly 128 and puck connector 130 to set a correct transfer gap if necessary.

With reference again to FIGS. 1-11, a process for reconfiguring the cutting and transfer apparatus 10 is now described here below according to an embodiment of the invention. With regard to the process described here below, it is recognized that only some of the described steps may need to be performed when reconfiguring the cutting and transfer apparatus 10, with the exact process that is implemented being determined by a revised new process flow and/or new product type/size to be processed by the cutting and transfer apparatus 10. Thus, it is to be understood that the process described here below is only meant to be an exemplary process and embodiments of the invention are not meant to be limited only to the described process.

When it is desirable to reconfigure the cutting and transfer apparatus 10 in order to implement a different process flow and/or accommodate a different product type/size, various components of the cutting and transfer apparatus 10 may be swapped out and/or repositioned. As a first step in such a process, the cutter mechanism 14 may be moved away from transfer mechanism 12 in order to provide easier access to components of each mechanism from an operator side of the apparatus 10. In moving the cutter mechanism 14, plate 20 to which cutter mechanism 14 is mounted is slid along rails 22 in a direction 24 to move the cutter mechanism 14 away from the transfer mechanism 12.

In a next step of the reconfiguring process, the anvil wheel 42 may be removed from the drive shaft 36 to which it is mounted and replaced with an anvil wheel 42 of a differing configuration. That is, an anvil wheel 42 with a different number of anvils 46 thereon may be substituted into the apparatus 10 based on any planned configuration changes made to the transfer mechanism 12 (i.e., adding/removing carriage units 28/pucks). It is recognized that it may be desirable to employ an anvil wheel 42 having the smallest diameter and smallest number of anvils 46 that will be suitable for use in the configured apparatus 10, so to maximize access to the apparatus—with anvil wheels 42 having a 3-up, 4-up, 5-up, 6-up, or 7-up anvil count being envisioned as being utilized in the apparatus 10, although it is recognized that are other configurations/counts could also be used.

In swapping in a desired anvil wheel 42 during the reconfiguration, it is recognized that repositioning of the anvil wheel 42 in the machine direction 89 may be required in order to accommodate the size change of the anvil wheel 42. That is, as a new anvil wheel 42 mounted on the drive shaft 54 may have a different diameter as compared to the anvil wheel 42 that was removed, the anvil wheel 42 may no longer be spaced apart from the knife roll 44 at a proper distance that would provide for cutting of an in-fed web. Therefore, as part of the reconfiguration, the anvil wheel 42 and drive shaft 54 to which it is mounted may be translated in the machine direction 89 along a track 142 provided on an anvil wheel stand 144 (FIG. 1) on which the anvil wheel 42 drive shaft is mounted. By translating the anvil wheel 42 and drive shaft 54 along track 142 in a desired direction and by a desired amount, the newly mounted anvil wheel 42 may be properly positioned relative to knife roll 44 so as to enable an interaction therebetween that cuts the web during operation of apparatus 10.

The reconfiguring process may continue with removal of the face cam plate 72 from the transfer mechanism 12. The face cam plate 72 is removed from its position on the drive shaft 36 in order to enable swapping out thereof with a face cam plate 72 having a different configuration and/or to provide access to the carriage units 28 of transfer mechanism 12. According to one embodiment, the face cam plate 72 is removed and swapped out for a face cam plate 72 having a pitch cam race 74 of a different size/configuration, so as to enable different velocity and pitch control of the pucks 30 of carriage units 28.

Figure 12:
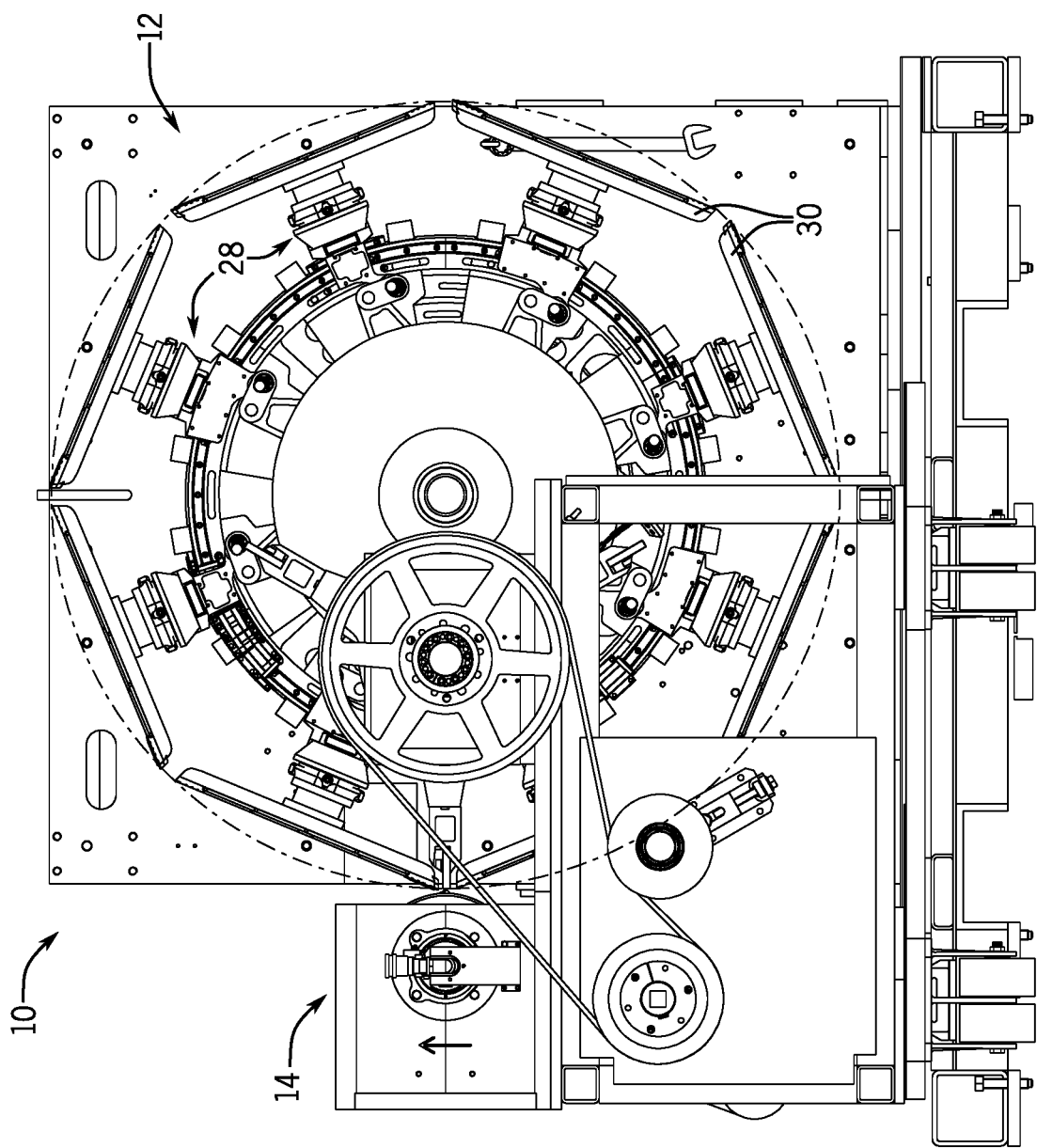
FIG. 12 is a front elevation view of a configurable cutting and transfer apparatus with a transfer mechanism including eight pucks, according to an embodiment of the invention.
Figure 13:
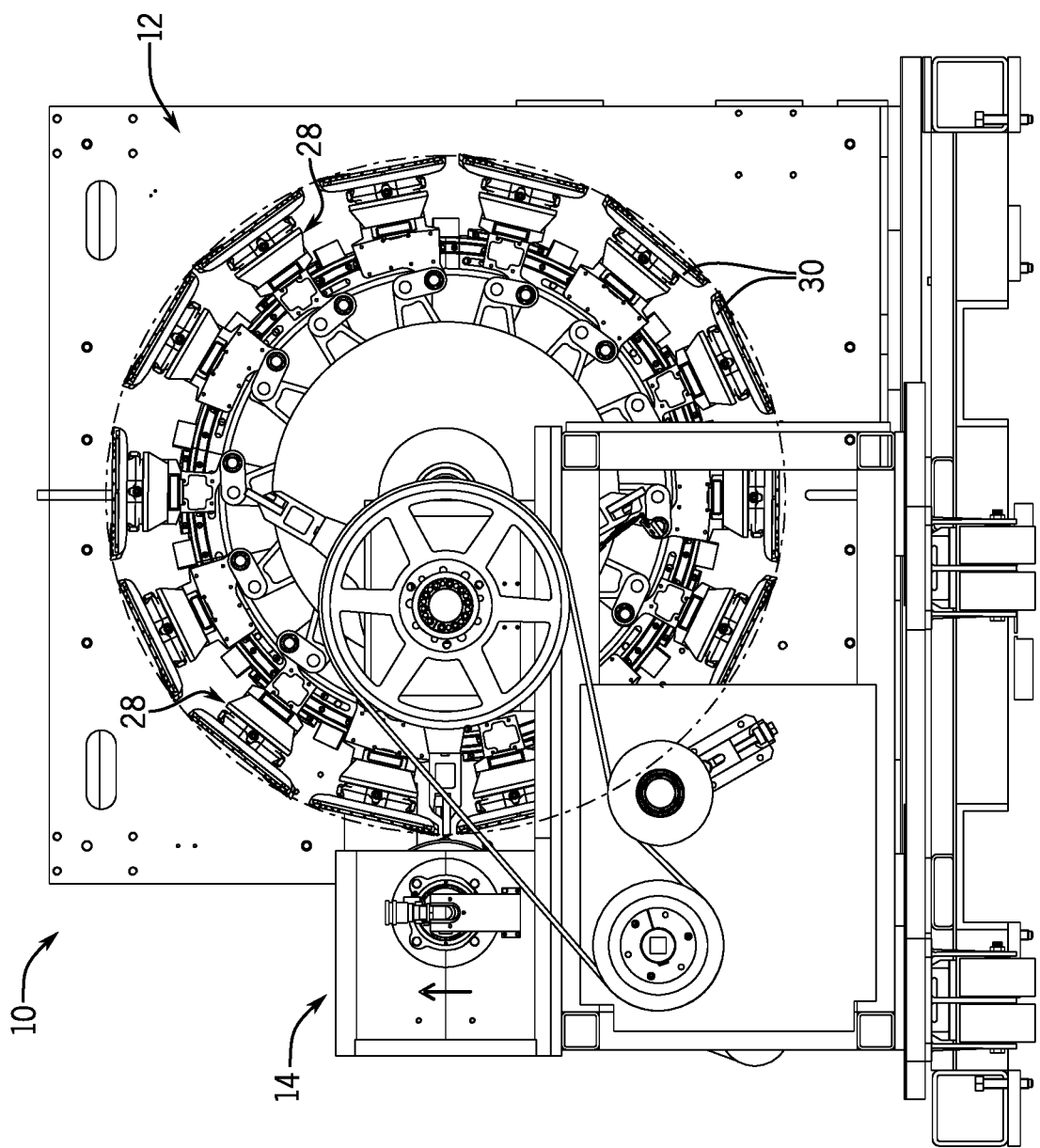
FIG. 13 is a front elevation view of a configurable cutting and transfer apparatus with a transfer mechanism including fourteen pucks, according to an embodiment of the invention.

Upon removal of the face cam plate 72, an operator is able to access the carriage units 28 of transfer mechanism 12—which are mounted to carriage plate 34 via a plurality of fasteners. In reconfiguring the transfer mechanism 12, an operator may then add or subtract carriage units 28 from the carriage plate 34 as desired in order to provide a desired number of carriage units 28 (and pucks 30). Depending on the number of carriage units 28 mounted to carriage plate 34, it is recognized that gaps 70 may be present between adjacent carriage units 28. These gaps 70 between adjacent carriage units 28 may be left open or, according to one embodiment, may be filled with spacers (not shown) that fits in the gaps and are secured to carriage plate 34. FIGS. 12 and 13 illustrate two cutting and transfer apparatuses 10 where the transfer mechanism 12 includes differing numbers of carriage unit 28—i.e., where eight carriage units 28 are included in transfer mechanism 12 (FIG. 12) and where fourteen carriage units 28 are included in transfer mechanism 12 (FIG. 13). The number of carriage units 28 mounted to carriage plate 34 will be dictated by the cutting and transferring process to be performed by apparatus 10, and will be based at least in part on the type/size of the inserts to be cut and transferred on the apparatus 10.

In addition to controlling the number of carriage units 28 to be included in transfer mechanism 12 when performing the reconfiguration, it is recognized that the individual pucks 30 included on the carriage units 28 may also be swapped out during the reconfiguration. Pucks 30 are constructed to include a puck connector 130 that slidingly engages a puck mount 90 to secure the puck 30 to the puck support 32 of a carriage unit 28. The structure of puck connector 130 and mating thereof with puck mount 90 allows for pucks 30 to be easily swapped out and exchanged on carriage unit 28 based on the specific set-up of the transfer mechanism 12. Different size pucks 30 can be connected to carriage units 28 to accommodate the cutting and transferring of articles of differing types and sizes.

Upon the reconfiguring of the cutting and transfer apparatus 10 and the swapping in and out of individual components thereof as desired, the apparatus may be reassembled and the cutter mechanism 14 moved backed into arrangement with the transfer mechanism 12. The apparatus 10 may thus be reconfigured to process products of a different type/size as compared to a previous set-up, with the reconfiguration being performed without having to swap out the entire transfer device 12 and/or individual heavy components thereof (i.e., base plate 60, barrel cam 82, etc.) and without having to employ specialized equipment. The reconfiguration may thus be performed in a quick and efficient manner where downtime of the cutting and transfer apparatus 10 is minimized.

Referring now to FIGS. 14-24, operation of the configurable cutting and transfer apparatus 10 is described in greater detail for purposes of better illustrating embodiments of the invention. The apparatus is illustrated with the transfer mechanism 12 including an arrangement of nine pucks 30 thereon, but it is recognized that operation of the apparatus would be the same with a greater or lesser number of pucks 30. Additionally, while operation of the apparatus 10 is described with reference to a single puck 30a and a single anvil 46a, it is to be understood that the operation of the remaining pucks 30 and anvils 46 is at least substantially similar. Furthermore, although the operation is described with reference, in FIGS. 17-24, to discrete puck positions, it is to be understood that the operation is preferably generally continuous. The discrete positions aid in illustrating the operations being performed.

Figure 14:
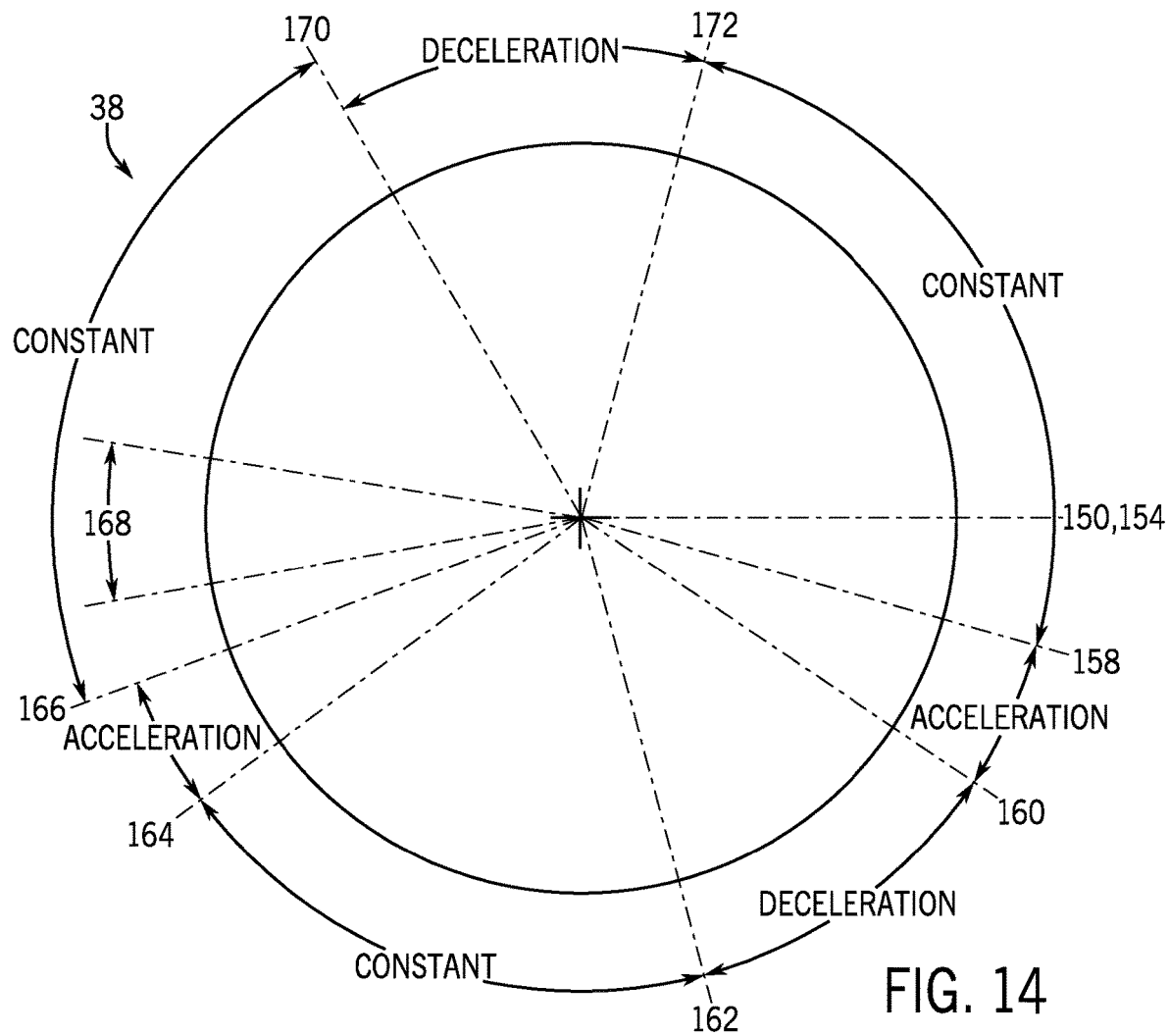
FIG. 14 is a front elevation schematic representation of a first preferred velocity profile of a configurable cutting and transfer apparatus, according to an embodiment of the invention.
Figure 15:
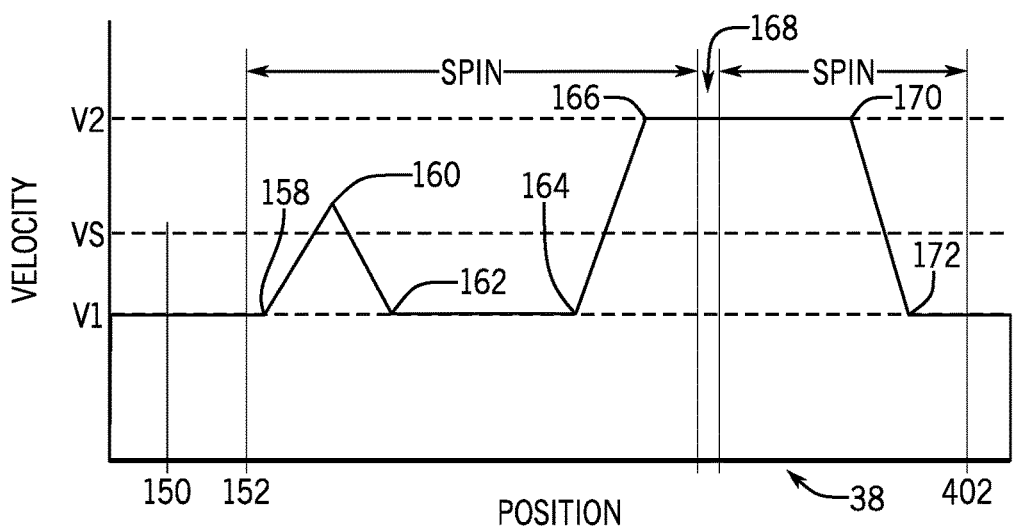
FIG. 15 is a graph view of the preferred velocity profile of FIG. 14.
Figure 16:
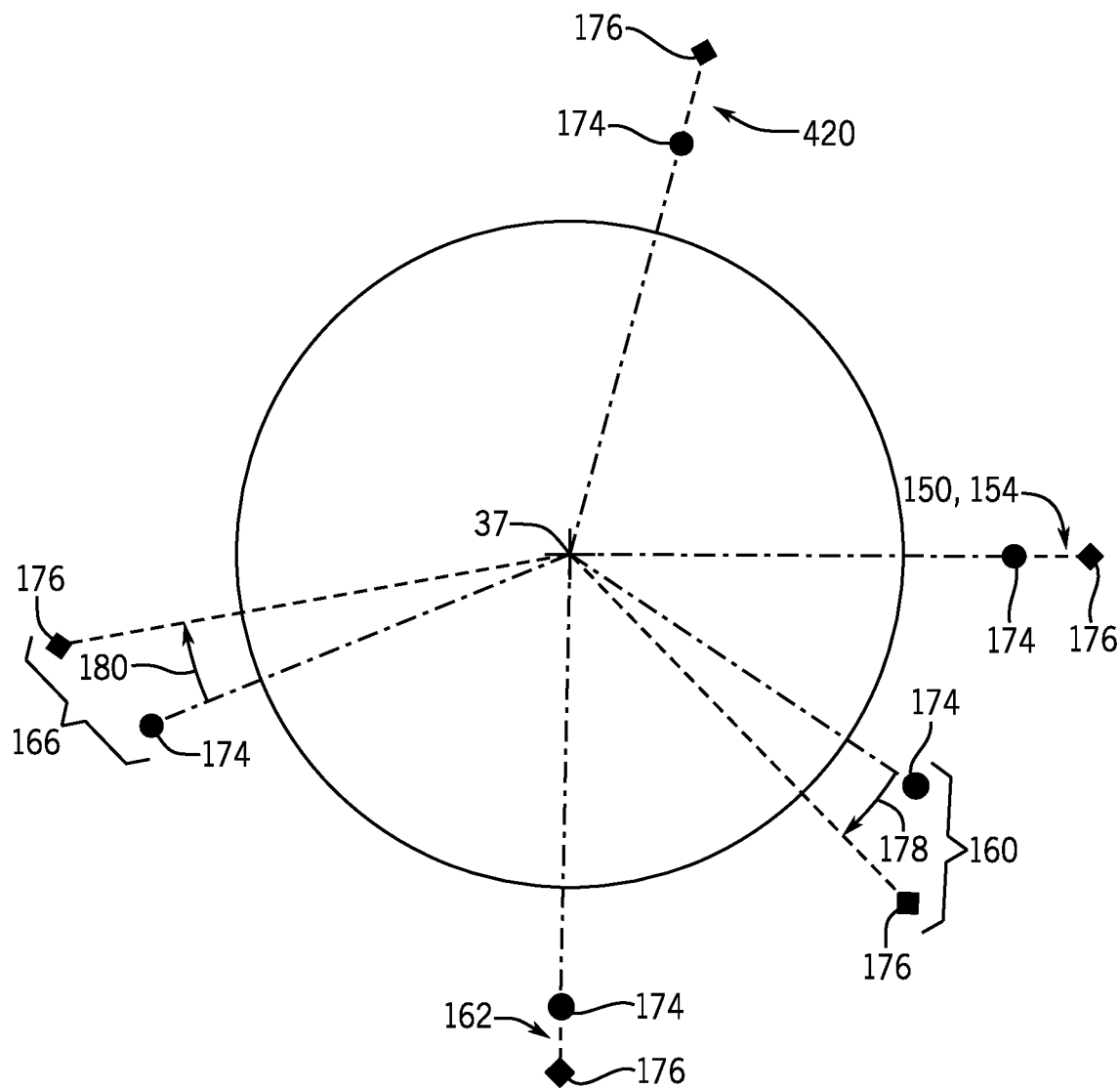
FIG. 16 is a front elevation schematic representation of puck position changing relative to a major axis of rotation, the puck following the velocity profile of FIG. 14.

Referring first to FIGS. 14 and 15, and with reference also to FIGS. 17-24, an exemplary puck velocity profile is depicted, as each puck 30 rotates through various portions of its transfer path 38. The puck transfer mechanism 12 rotates about the puck transfer axis 37 at a relatively constant velocity VS. When a puck 30 receives a continuous web material 146, the puck 30 may be moving at a substantially constant first velocity V1. A pad 148 is then cut from the continuous web 146. To create the pad 148, a first cut 150 is made proximate a leading puck edge 152 and a second cut 154 is made proximate the trailing puck edge 156. Just after a pad 148 is cut from the web material 146, the puck 30 may be accelerated 158 to prevent any collision with the subsequent neighboring puck 30 and may be decelerated 160 thereafter back to a substantially constant velocity 162, which may be the first velocity V1. Sometime after the trailing edge cut 154 and prior to placement 168 of the pad 148 on a receiving surface 140, the puck 30 spins to a desired angle and the velocity of the puck 30 may change 164 to achieve a desirable predetermined circumferential spacing. Upon or after reaching a substantially constant 166 second velocity V2, the pad 148 is placed 168 on the receiving surface 140. After pad placement 168, the puck 30 is decelerated 170 to a substantially constant 172 first velocity V1 and is spun back to a web-receiving orientation. The process then begins anew.

During periods of acceleration and deceleration, the pucks 30 change position relative to the major axis of rotation, the puck transfer axis 37. This can best be seen by reference to FIG. 16. A first reference point 174 represents a point on the shaft 36 (FIG. 1) spinning about the puck transfer axis 37 at the relatively constant velocity VS during operation of the transfer mechanism 12. A second reference point 176 represents a position of a puck 30. While the shaft reference 174 may be rotating about the puck transfer axis 37 at a constant velocity, the position of the puck reference 176 with respect to the shaft 36 may change a desirable amount, such as an increase of ten degrees or more of rotation during acceleration and a decrease of ten degrees or more of rotation during deceleration. To illustrate, the shaft reference 174 is generally radially aligned with the puck reference 176 during times of cutting 150, 154. At the end 160 of the first acceleration, the puck reference 176 has changed position relative to the shaft reference 174 by a first distance 178. At the end 162 of the first deceleration period, the references 174, 176 are again aligned. Prior to pad placement 168, the puck 30 is again accelerated, and at the end 166 of the second acceleration the puck reference 176 has advanced beyond the shaft reference 174 by a second distance 180. The first distance 178 may be the same as, or different than, the second distance 180. Finally, at the end 172 of the second deceleration period, both references 174, 176 are aligned and ready for another revolution.

FIG. 17 shows a representative puck 30a in a first position P1. In the first position P1, the puck 30a receives continuous web material 146 traveling in a first direction 182 at the first velocity. A vacuum is drawn through the carriage unit 28 (through mounting block 66, puck support 32, and the puck 30a) to support the web material 146 on the puck 30a surface. While receiving the web 146, the puck 30a is traveling about a puck transfer axis 37 in a second direction 89 (i.e., machine direction), to which at this point P1 the first direction 182 is preferably substantially tangential. The puck 30a continues to move in the second direction 89 into a second position P2.

Figure 18:
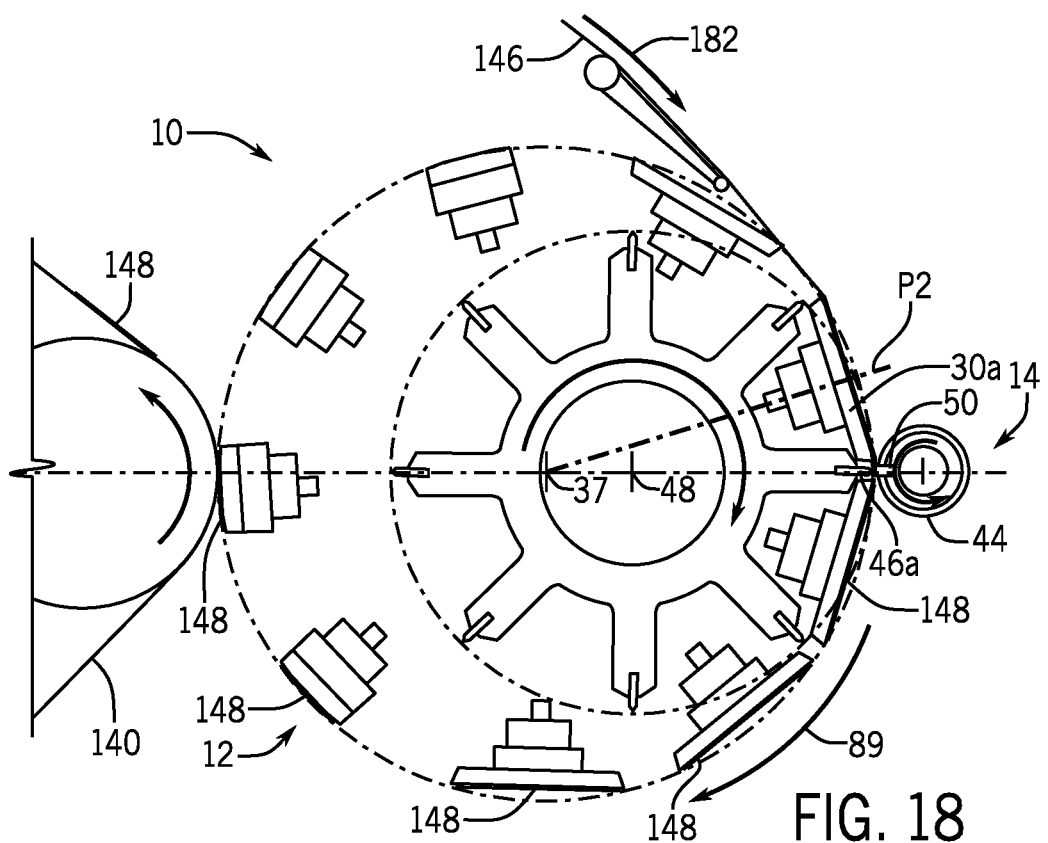
FIG. 18 is a front elevation view of the apparatus of FIG. 17 in a second position, eliminating some detail to better illustrate functionality.

FIG. 18 depicts the puck 30a in the second position P2. In this position, the puck 30a is at the leading edge cut time 150 of FIG. 14. Here, a knife blade 50 of knife roll 44 cooperates with a representative anvil 46a of the anvil wheel 42 to cut the web 146 proximate the leading edge 152 of the puck 30a. After receipt of the web 146 and the cut made near the leading edge 152, the puck 30a proceeds to travel in the second direction 89 past the knife roll 44 to a third position P3.

Figure 19:
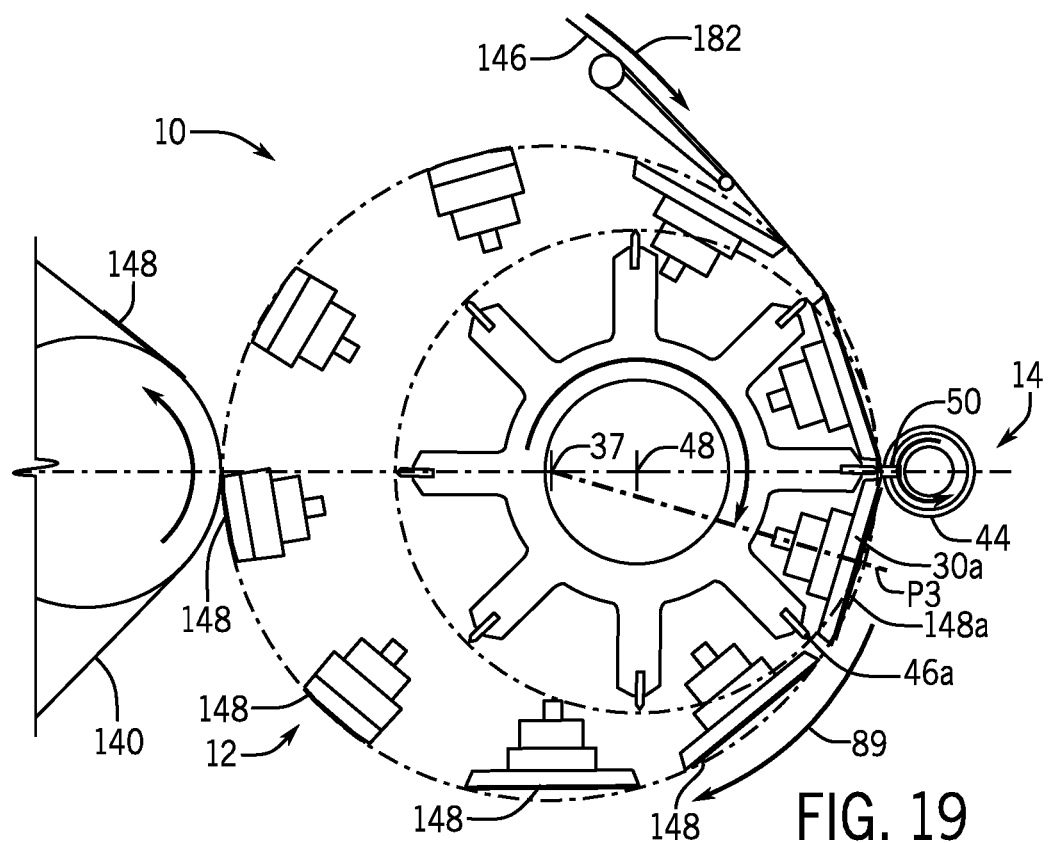
FIG. 19 is a front elevation view of the apparatus of FIG. 17 in a third position, eliminating some detail to better illustrate functionality.

FIG. 19 shows the puck 30a in the third position P3. In this position P3, the puck 30a is at the trailing edge cut time 154 of FIG. 6. In this position P3, a knife blade 50 of knife roll 44 cooperates with an anvil 46 to cut the web 146 proximate the trailing edge 156 of the puck 30a to cut a section 148a from the web 146. The section 148a is held to the puck 30a by the vacuum, which was drawn previously. After the cut made near the trailing edge 304a, the puck 30a proceeds to travel in the second direction 89 to a fourth position P4.

Figure 20:
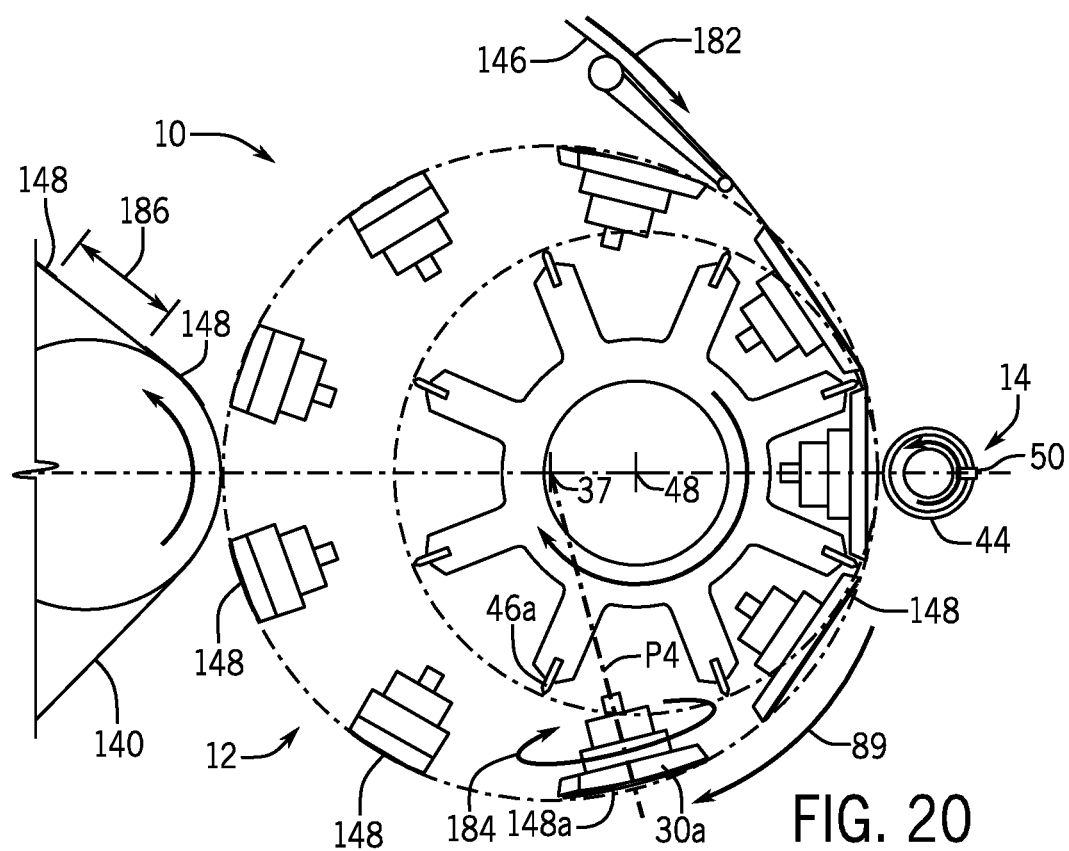
FIG. 20 is a front elevation view of the apparatus of FIG. 17 in a fourth position, eliminating some detail to better illustrate functionality.
Figure 21:
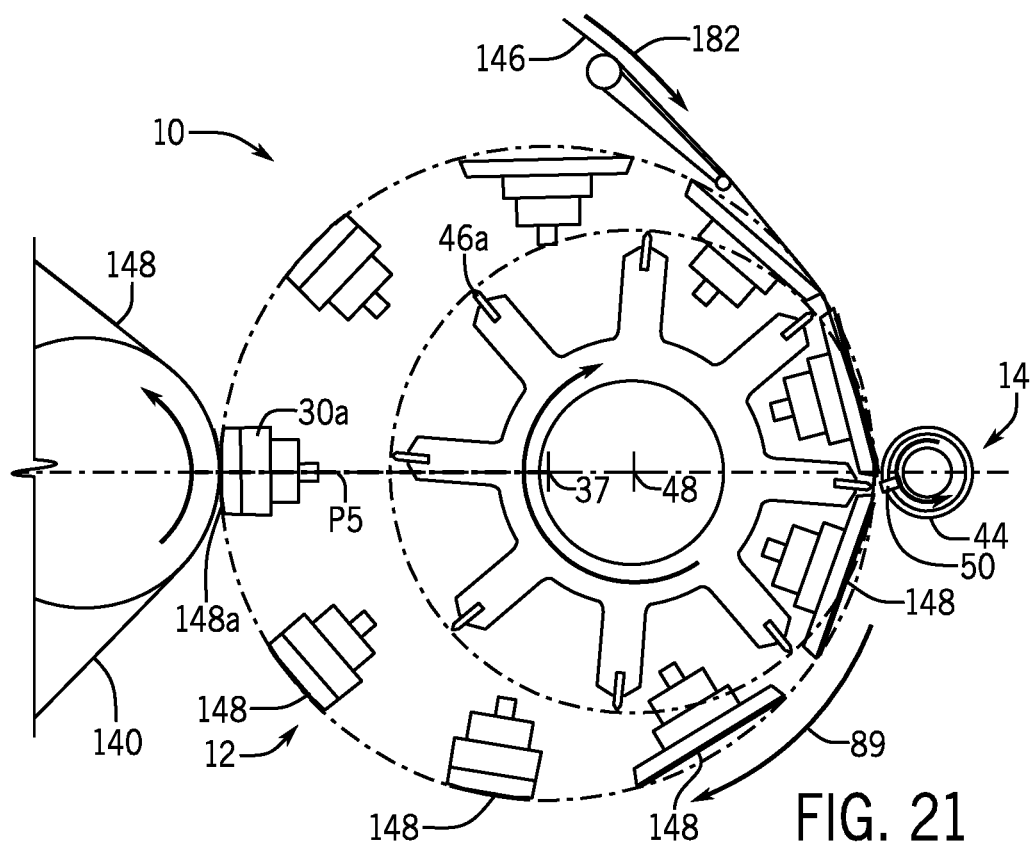
FIG. 21 is a front elevation view of the apparatus of FIG. 17 in a fifth position, eliminating some detail to better illustrate functionality.

FIG. 20 shows the puck 30a in the fourth position P4. As mentioned previously, it is often desirable to spin the cut section 148a to some predetermined angle prior to placement on a receiving surface 140. Here, the puck 30a is shown while in the midst of a spin. While FIG. 20 shows the puck 30a rotating in the fourth position P4, the puck 30a may rotate in a third direction 184 to a desired angle any time after the trailing edge cut made at the third position P3 and before placement onto the receiving surface 140.

Besides rotation and spin of the pucks 30, the apparatus 10 may also change the circumferential spacing of the pucks 30a; thereby resulting in a placement pitch that is different from the pitch at which the web material 146 was cut. The eccentric nature of the puck transfer axis 37 and the anvil wheel axis 48 allows the puck 30a to drop away from the anvil wheel 42, thereby providing greater angular movement ability than if an anvil 46 remained between consecutive pucks 30. The ultimate circumferential spacing of the pucks 30 at the receiving surface 140 is a function of a desired placement pitch 186 and the speed at which the receiving surface 140 is traveling. In the preferred embodiment, the circumferential spacing is achieved by a desired pitch cam race 74 configuration. Although the terms "circumferential" and "rotation" are used to describe the transfer movement of the pucks 30 herein, it is to be understood that the invention is not limited to applications utilizing a circular motion and that the transfer path 38 of the pucks 30 may be defined by the shape of an employed cam plate or by the path of any supporting pitch rails used, for example.

Upon achieving desired circumferential spacing, the puck 30a arrives in a fifth position P5. The puck 30a is shown in the fifth position P5 in FIG. 21. In this position P5, the puck 30a is at the middle of the placement time 168 shown in FIG. 14. The puck 30a has been situated at the correct placement pitch or distance 186 with respect to the puck 30 that preceded it 301a. At this pitch or distance 186, the section 148a is transferred to the receiving surface 140. At the time of placement, the vacuum that was drawn through the puck support 32 and puck 30a may be removed from at least a portion of the puck 30a, thereby allowing a smooth transfer of the cut insert 148a from the puck 30a to the receiving surface 140. After placing the section 148a onto the receiving surface 140, the puck 30a continues in the second direction 89 to a sixth position P6.

Figure 22:
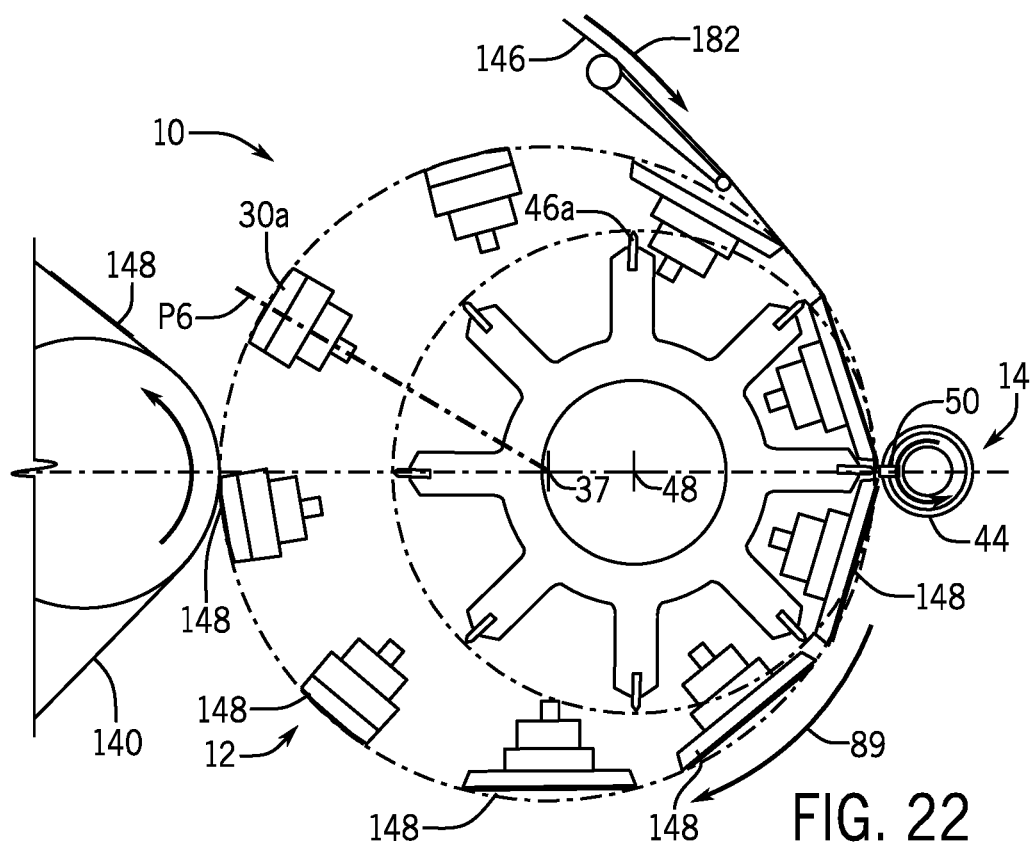
FIG. 22 is a front elevation view of the apparatus of FIG. 17 in a sixth position, eliminating some detail to better illustrate functionality.

FIG. 22 shows the puck 30a in the sixth position P6. The puck 30a is shown as having released the cut section 148a onto the receiving surface 140. The puck 30a continues to move in the second direction 89 to a seventh position.

Figure 23:
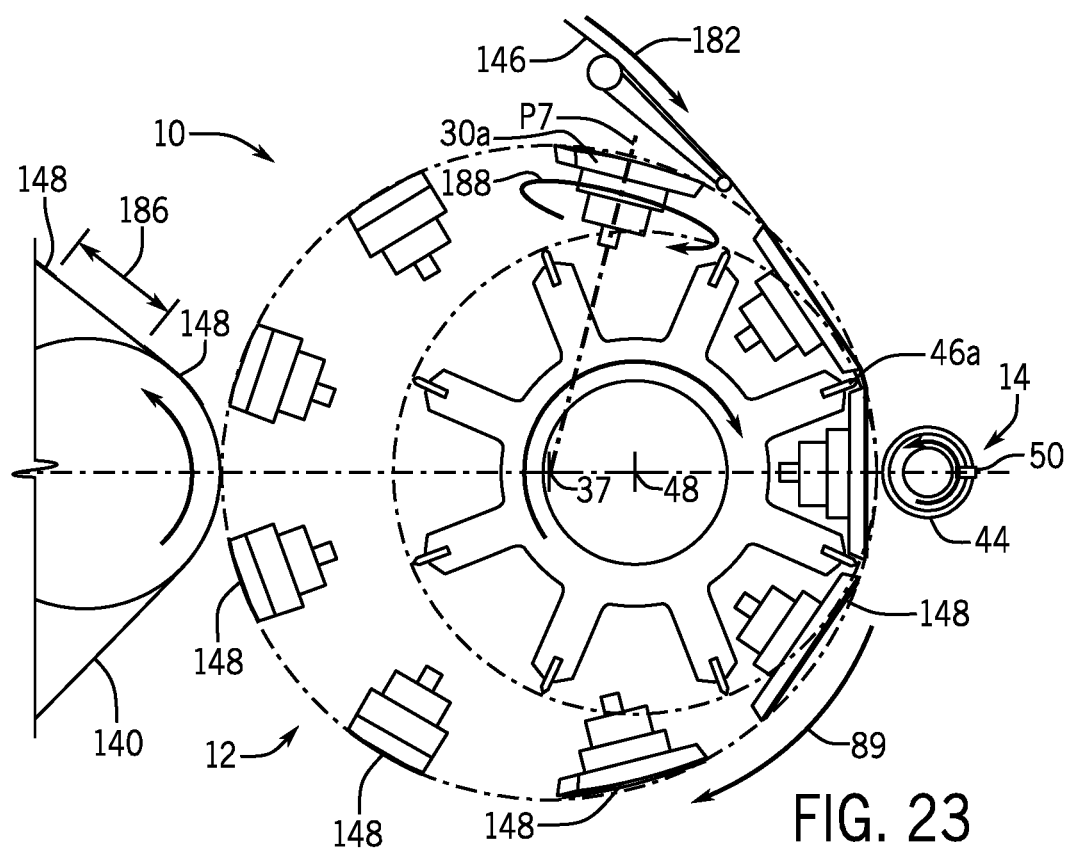
FIG. 23 is a front elevation view of the apparatus of FIG. 17 in a seventh position, eliminating some detail to better illustrate functionality.

FIG. 23 depicts the seventh position P7 of the puck 30a. If the puck 30a and pad 148a were rotated after cutting to some predetermined angle prior to placement on the receiving surface 140, the puck 30a may need to be adjusted to a web-receiving orientation. While FIG. 23 shows the puck 30a spinning in the seventh position P7, the puck 30a may spin in a fourth direction 188 any time after the section 148a has been placed on the receiving surface 140 and before the continuous web 146 is received. The fourth direction 188 may be the same as the third direction 184 or different.

Figure 24:
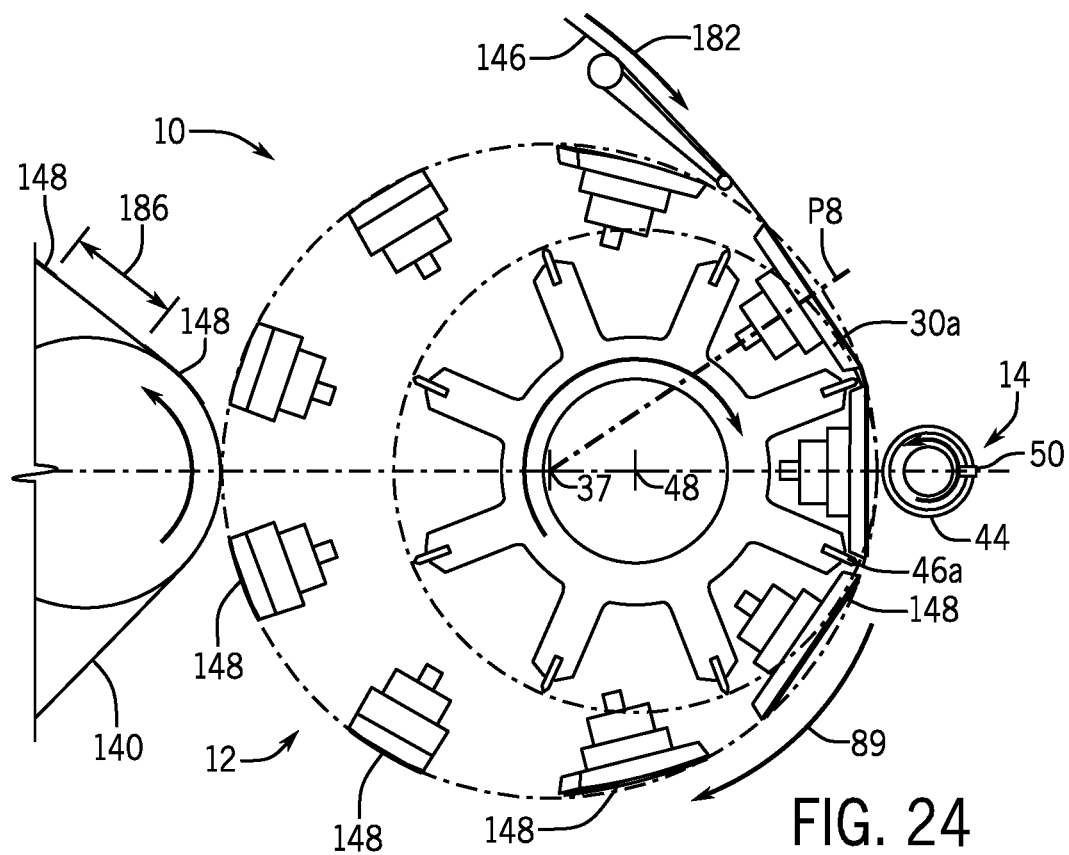
FIG. 24 is a front elevation view of the apparatus of FIG. 17 in an eighth position, eliminating some detail to better illustrate functionality.

Finally, the puck 30a is shown in the eighth position P8 in FIG. 24. The eighth position P8 is substantially similar to the first position P1, except that the anvil 46a has now advanced a number of positions ahead of the puck 30a. The number of positions advanced is a function of the difference between the number of pucks 30 and the number of anvils 46. In this operating example, there are nine pucks 30 and eight anvils 46. Therefore, in the eighth position P8, the anvil 46a has advanced one position ahead of its position in the first position P1.

It is recognized that the operation of the configurable cutting and transfer apparatus 10 shown and described above in FIGS. 14-24, including the described puck velocity profile, is for illustrative purposes only. That is, the rotation of the pucks about the transfer path may follow a different suitable velocity profile and/or spinning of the pucks may vary from that described, according to additional embodiments of the invention, and that such embodiments are recognized as falling within the scope of the invention.

Beneficially, embodiments of the invention thus provide a configurable cutting and transfer apparatus, and method of configuring and operating such an apparatus, so as to provide for adjustments in operation of the apparatus to accommodate cutting and transferring of articles of differing types and sizes. The apparatus provides for the selective addition/removal of carriage units and associated pucks from the transfer mechanism, as well as the swapping of pucks on each carriage unit. Additionally, the anvil wheel and knife in the cutting mechanism may be configured and positioned in a selected manner to correspond to any changes to the transfer mechanism, so as to provide for cutting of a continuous web into discrete articles/pads to be carried on the transfer device. Such reconfiguring of the cutting and transfer apparatus may be done without the use of specialized equipment and may be performed in a quick and efficient manner where downtime of the cutting and transfer apparatus is minimized.

Therefore, according to one embodiment of the invention, a configurable cutting and transfer apparatus includes a cutter mechanism configured to cut an incoming web of material into a plurality of discrete articles and a transfer mechanism operable with the cutter mechanism to transfer and rotate the plurality of discrete articles from at least a web receiving location to an article placement location. The transfer mechanism further includes a drive shaft rotatable about a transfer axis, a carriage plate mounted to the drive shaft so as to rotate therewith about the transfer axis, and a segmented puck wheel comprising a plurality of carriage units securable to, and repositionable on, the carriage plate so as to rotate therewith to travel along a transfer path about the transfer axis from at least the web receiving location to the pad placement location, each of the plurality of carriage units including a puck that is selectively operable to provide a rotating and re-pitching of the articles between the web receiving location and the pad placement location.

According to another embodiment of the invention, a method for configuring a configurable cutting and transfer apparatus includes providing a cutter mechanism configured to cut an incoming web of material into a plurality of discrete articles and providing a transfer mechanism operable with the cutter mechanism to transfer and rotate the plurality of discrete articles from at least a web receiving location to an article placement location. Providing the transfer mechanism further includes providing a drive shaft having a carriage plate mounted thereto, the drive shaft and carriage plate rotatable about a transfer axis and mounting a plurality of carriage units to the carriage plate to form a segmented puck wheel, the plurality of carriage units rotatable with the carriage plate to travel along a transfer path about the transfer axis from at least the web receiving location to the pad placement location, with each of the plurality of carriage units including a puck operable to provide a rotating and re-pitching of the articles between the web receiving location and the pad placement location. A construction of the carriage plate and the plurality of carriage units enables mounting of the plurality of carriage units in a plurality of arrangements and in various numbers on the carriage plate, so as to provide a configurable cutting and transfer apparatus.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A configurable cutting and transfer apparatus comprising:
   a cutter mechanism having a rotating knife, configured to cut an incoming web of material into a plurality of discrete articles; and
   a transfer mechanism operable with the cutter mechanism to transfer and rotate the plurality of discrete articles from at least a web receiving location to an article placement location, the transfer mechanism comprising:
      a drive shaft rotatable about a transfer axis;
      a carriage plate formed as a ring having a continuous flat radially directed surface about a circumference thereof, the continuous flat surface having a plurality of mounting holes formed therein, the carriage plate mounted to the drive shaft so as to rotate therewith about the transfer axis;
      a segmented puck wheel comprising a plurality of carriage units securable to, and repositionable on, the carriage plate so as to rotate therewith to travel along a transfer path about the transfer axis from at least the web receiving location to the pad placement location, each of the plurality of carriage units including a puck that is selectively operable to provide a rotating and re-pitching of the articles between the web receiving location and the pad placement location;
a barrel cam stationarily situated about the transfer axis and positioned on aside of the carriage plate opposite the segmented puck wheel, the barrel cam having a spincam race therein around a circumference thereof; and
wherein a variable number of carriage units are mounted at selectable spacings about the continuous flat surface of the carriage plate via the mounting holes.

2. The apparatus of claim 1 wherein the transfer mechanism comprises:
a face cam plate stationarily situated about the transfer axis and positioned on a side of the segmented puck wheel opposite the carriage plate, the face cam plate having a pitch cam race therein on a side of the face cam plate facing the segmented puck wheel.

3. The apparatus of claim 2 wherein each of the plurality of carriage units comprises:
a pitch cam follower in sliding or rolling communication with the pitch cam race to alter positioning of the pucks with respect to the segmented puck wheel along at least a portion of the transfer path; and
a spin cam follower in sliding or rolling communication with the spin cam race to spin the puck at least partially about a spin axis of the respective puck that is at least substantially perpendicular to the transfer axis.

4. The apparatus of claim 3 wherein each of the plurality of carriage units comprises:
a mounting block secured to the carriage plate, the mounting plate including a pair of pitch rails secured thereto that are oriented parallel to a direction of the transfer path;
a puck support positioned on the mounting block and movable relative thereto via a mating of rail guides of the puck support the with the pitch rails, the puck support oriented generally orthogonal to the pitch rails and comprising a puck mount on one end thereof that is configured to receive the puck; and
a linkage system operatively coupled to the puck support and to the pitch cam follower to transfer movement of the pitch cam follower to the puck support, so as to cause movement of the puck support along the pitch rails and thereby alter circumferential displacement of the puck with respect to the carriage unit along at least a portion of the transfer path.

5. The apparatus of claim 4 wherein the carriage plate includes a plurality of mounting holes arranged as two concentric circles on the carriage plate, and wherein the mounting plate of each respective carriage unit comprises fastener holes arranged so as to be alignable with a number of the mounting holes on the carriage plate to provide for positioning of fasteners therethrough to secure the carriage unit to the carriage plate at a desired location.

6. The apparatus of claim 4 wherein the puck support in each of the plurality of carriage units comprises:
a spin cam follower holder configured to house a portion of the spin cam follower therein; and
a belt operatively coupled to the puck support and to the spin cam follower to transfer movement from the spin cam follower to the puck mount, so as to cause the puck mounted to the puck support to spin about the spin axis.

7. The apparatus of claim 4 wherein the transfer mechanism comprises a base plate positioned about the carriage plate and coupled to the barrel cam; and
wherein the carriage unit comprises:
a vacuum plate positioned between a portion of the mounting block and the base plate, the vacuum plate included one or more openings formed therein that provide an air passage into and out from the puck support; and
vacuum channels formed in the puck support to form a fluid flow path from the vacuum plate openings to the puck mount and the puck mounted thereon.

8. The apparatus of claim 7 wherein the vacuum channels are fluidly coupled to multiple vacuum zones on the puck, and wherein an orientation of the puck about the spin axis controls a fluid communication between the vacuum channels and the multiple vacuum zones, so as to selectively enable a pick-up and transfer of a respective article to and from the puck.

9. The apparatus of claim 1 wherein the puck of each respective carriage unit comprises a puck connector coupleable with the puck mount, the puck connector comprising a quick-connect connector configured to secure the puck to the puck mount.

10. The apparatus of claim 9 further comprising one or more shim spacers positioned on the puck connector, the one or more shim spacing increasing a height that the puck extends out from the puck support.

11. The apparatus of claim 1 wherein the cutter mechanism comprises:
a first cutter component, a majority of which is situated within the transfer path; and
a second cutter component, a majority of which is situated outside the transfer path, the second cutter component adapted to periodically cooperate with the first cutter component to form a cutting nip.

12. The apparatus of claim 11 wherein the first cutter component comprises an anvil wheel comprising a plurality of anvils spaced circumferentially about an anvil wheel axis, the anvil wheel driven by a drive shaft to rotate about the anvil wheel axis; and
wherein the second cutter component comprises a knife roll including one or more knives thereon, the one or more knives periodically cooperating with the anvils to form the cutting nip.

13. The apparatus of claim 12 wherein the anvil wheel and drive shaft are mounted on an anvil wheel stand, the anvil wheel stand comprising a track along which the anvil wheel and drive shaft may be translated to alter a distance between the anvil wheel and knife roll.

14. The apparatus of claim 1 further comprising a base frame on which each of the cutter mechanism and transfer mechanism are mounted, the base frame comprising a pair of rails along which at least one of the cutter mechanism and transfer mechanism is movable to increase a distance between the cutter mechanism and the transfer mechanism.

15. A method for configuring a configurable cutting and transfer apparatus, the method comprising:
providing a cutter mechanism having a rotating knife, configured to cut an incoming web of material into a plurality of discrete articles; and
providing a transfer mechanism operable with the cutter mechanism to transfer and rotate the plurality of discrete articles from at least a web receiving location to an article placement location, wherein providing the transfer mechanism comprises:
providing a drive shaft having a carriage plate mounted thereto, the drive shaft and carriage plate rotatable about a transfer axis, wherein the carriage plate is formed as a ring having a continuous flat radially directed surface about a circumference thereof, the continuous flat surface having a plurality of mounting holes formed therein; and mounting a plurality of carriage units to the mounting holes of carriage plate to form a segmented puck wheel, the plurality of carriage units rotatable with the carriage plate to travel along a transfer path about the transfer axis from at least the web receiving location to the pad placement location, with each of the plurality of carriage units including a puck operable to provide a rotating and re-pitching of the articles between the web receiving location and the pad placement location;

providing a barrel cam stationarily situated about the transfer axis and positioned on aside of the carriage plate opposite the segmented puck wheel, the barrel cam having a spincam race therein around a circumference thereof;

wherein a construction of the carriage plate and the plurality of carriage units enables mounting of the plurality of carriage units in a plurality of arrangements and in various numbers on the carriage plate, so as to provide a configurable cutting and transfer apparatus, and wherein the carriage plate includes a plurality of mounting holes arranged on the carriage plate, wherein the arrangement of mounting holes is such that the carriage plate may receive a varying number of different carriage units thereon at differing locations and at different spacings.

16. The method of claim 15 wherein mounting the plurality of carriage units to the carriage plate comprises aligning fastener holes on each of the plurality of carriage units with fastener holes in the carriage plate for receiving fasteners therethrough to mount the plurality of carriage units to the carriage plate, the fastener holes on the carriage plate arranged as two concentric circles on the carriage plate.

17. The method of claim 15 wherein providing the transfer mechanism comprises:

providing a face cam plate that is stationarily situated about the transfer axis and positioned on a side of the segmented puck wheel opposite the carriage plate, the face cam plate having a pitch cam race therein on a side of the face cam plate facing the segmented puck wheel; and operatively coupling a pitch cam follower of each of the plurality of carriage units with the pitch cam race to enable altering of a positioning of the pucks with respect to the segmented puck wheel along at least a portion of the transfer path; and operatively coupling a spin cam follower of each of the plurality of carriage units with the spin cam race to enable spinning of the pucks at least partially about respective spin axes of the pucks that are at least substantially perpendicular to the transfer axis.

18. The method of claim 15 wherein, in providing the rotating and re-pitching of the articles between the web receiving location and the pad placement location for the puck of a respective carriage unit, the method comprises:

operatively coupling the pitch cam follower to a puck support having the puck mounted thereon to transfer movement of the pitch cam follower to the puck support and thereby alter circumferential displacement of the puck with respect to the carriage unit along at least a portion of the transfer path; and operatively coupling the spin cam follower to the puck support to transfer movement of the spin cam follower to the puck so as to cause the puck mounted to the puck mount to spin about the spin axis.

19. The method of claim 18 wherein operatively coupling the pitch cam follower to the puck support comprises:

providing a pair of pitch rails in the carriage unit that are oriented parallel to a direction of the transfer path;

slidingly coupling the puck support to the pair of pitch rails via rail guides on the puck support; and operatively coupling the puck support to the pitch cam follower via a linkage system of the carriage unit, such that movement of the pitch cam follower is transferred to the puck support via the linkage system and causes movement of the puck support along the pitch rails to alter circumferential displacement of the puck with respect to the carriage unit.

20. The method of claim 19 further comprising providing one or more shim spacers in the puck to increase a height that the puck extends out from the puck support.

21. The method of claim 18 wherein operatively coupling the spin cam follower to the puck support comprises operatively coupling the spin cam follower to a belt on the puck support, the belt transferring movement from the spin cam follower to a puck mount of the puck support to which the puck is mounted, so as to cause the puck mounted to the puck mount to spin about the spin axis.

22. The method of claim 15 further comprising coupling the puck of each respective carriage unit to a puck support of the carriage unit, the puck mounted on a puck mount of the puck connector via a quick-connect connection.

23. A configurable cutting and transfer apparatus comprising:

a cutter mechanism having a rotating knife configured to cut an incoming web of material into a plurality of discrete articles; and a transfer mechanism operable with the cutter mechanism to transfer and rotate the plurality of discrete articles from at least a web receiving location to an article placement location, the transfer mechanism comprising:

a drive shaft rotatable about a transfer axis;

a carriage plate mounted to the drive shaft so as to rotate therewith about the transfer axis; and a segmented puck wheel comprising a plurality of carriage units securable to, and repositionable on, the carriage plate so as to rotate therewith to travel along a transfer path about the transfer axis from at least the web receiving location to the pad placement location, each of the plurality of carriage units including a puck that is selectively operable to provide a rotating and re-pitching of the articles between the web receiving location and the pad placement location;

a face cam plate stationarily situated about the transfer axis and positioned on a side of the segmented puck wheel opposite the carriage plate, the face cam plate having a pitch cam race therein on a side of the face cam plate facing the segmented puck wheel; and a barrel cam stationarily situated about the transfer axis and positioned on aside of the carriage plate opposite the segmented puck wheel, the barrel cam having a spincam race therein around a circumference thereof.

* * * * *